United States Patent [19]
Cohen et al.

[11] Patent Number: 5,939,284
[45] Date of Patent: Aug. 17, 1999

[54] PROTEIN PHOSPHATASE 1 BINDING PROTEIN, R5

[75] Inventors: Patricia T. W. Cohen; Phillip Cohen, both of Dundee, United Kingdom; Peter R. Young, Lawrenceville, N.J.

[73] Assignee: Smithkline Beecham Corporation, Philadelphia, Pa.

[21] Appl. No.: 08/767,096

[22] Filed: Dec. 5, 1996

[51] Int. Cl.$^6$ .......................... C07H 21/04; C12N 15/12; C12N 15/63
[52] U.S. Cl. .................... 435/69.1; 536/23.1; 536/24.31; 435/320.1; 435/325; 435/252.3; 435/172.3
[58] Field of Search .................................. 536/23.1, 24.1; 435/69.1, 172.3, 320.1, 32.5, 252.33

[56] References Cited

PUBLICATIONS

Auffray et al. Image: Integration Au Niveau Moleculaire De L'Analyse Du Genome Humain Et De Son Expression C.R. Acad. Sci III, Sci Vie 318(2) pp. 363–272, 1995.
Promega Protein Guide: Tips and Techniques Promega Corporation, Madison, WI. USA pp. 55–65, 1993.
Yu Hua Chen et al., 37 Sequence of the Human Glycogen–Associated Regulatory Subunit of Type 1 Protein Phosphatase and Analysis of Its Coding Region and mRNA Level in Muscle From Patients With NIDDM, Diabetes, vol. 43, pp. 1234–1241, Oct., 1994.
Paul Dent et al., "The molecular mechanism by which insulin stimulates glycogen synthesis in mammalian skeletal muscle", Nature, vol. 348, pp. 302–308, Nov. 22, 1990.
Pauline M. Tang et al., "Molecular Cloning and Expression of the Regulatory ($R_{G1}$) Subunit of the Glycogen–associated Protein Phosphatase", J. of Biol. Chem., vol. 266 (24), pp. 15782–15789 (1991).
Sara Nakielny et al., "The molecular mechanism by which adrenalin inhibits glycogen synthesis", Eur. J. Boichem. vol. 199, pp. 713–722 (1991).
Greg Moorhead et al., "Purification of the hepatic glycogen–associated form of protein phosphatase–1 by microcystin– Sepharose affinity chromatography", FEBS Letters, vol. 362, pp. 101–105 (1995).
Martin J. Doherty et al., "Amino acid sequence and expression of the hepatic glycogen–binding ($G_L$)–subunit of protein phosphatase–1", FEBS Letters, vol. 375, pp. 294–298 (1995).
Dario Alessi et al., "The control of protein phosphatase–1 by targetting subunits", Eur. J. Biochem., vol. 210, pp. 1023–1035 (1992).
Paul Dent et al., "A myofibrillar protein phosphatase from rabbit skeletal muscle contains the β isoform of protein phosphatase–1 complexed to a regulatory subunit which greatly enhances the dephosphorylation of myosin", Eur. J. Biochem., vol. 210, pp. 1037–1044, (1992).
Yu Hua Chen et al., "Molecular cloning of cDNA encoding the 110 kDa and 21 kDa regulatory subunits of smooth muscle protein phosphatase 1M", FEBS Letters vol. 356, pp. 51–55 (1994).

Nichols R. Helps et al., "Protein phosphatase 1 interacts with p53BP2, a protein which binds to the tumour suppressor p53", FEBS Letters, vol. 377, pp. 295–300 (1995).
Aleyde Van Eynde et al., "Molecular Cloning of NIPP–1, a Nuclear Inhibitor of Protein Phosphatase–1, Reveals Homology with Polypeptides Involved in RNA Processing", J. of Biol. Chem., vol. 270 (47), pp. 28068–28074, Nov. 24, 1995.
Katsuya Hirano et al., "Interaction of protein phosphatase type 1 with a splicing factor", FEBS Letters, vol. 389, pp. 191–194 (1996).
Tim Durfee et al., "The retinoblastoma protein associates with the protein phosphatase type 1 catalytic subunit", Genes & Development, vol. 7, pp. 555–569 (1993).
Katsuya Hirano et al., "Interaction of the Ribosomal Protein, L5, with Protein Phosphatase Type 1", J. Biol. Chem., vol. 270 (34), pp. 19786–19790, Aug. 25, 1995.
Monique Beullens et al., "Characterization of a ribosomal inhibitory polypeptide of protein phosphatase–1 from rat liver", Eur. J. Biochem. vol. 239, pp. 183–189 (1996).
Izabela Jagiello et al., "Subunit Structure and Regulation of Protein Phosphatase–1 in Rat Liver Nuclei", J. of Biol. Chem., vol. 270 (29), pp. 17257–17263, Jul. 21, 1995.
Durio R. Alessi et al., "Inhibitor–2 functions like a chaperone to fold three expressed isoforms of mammalian protein phosphatase–1 into a conformation with the specificity and regulatory properties of the native enzyme", Eur. J. Biochem., vol. 213, pp. 1055–1066 (1993).
Deborah F. Johnson et al., "Identification of protein–phosphatase–1 binding domains on the glycogen and myofibrillar targetting subunits", Eur. J. Biochem., vol. 239, pp. 317–325 (1996).
Philip Cohen, "The Structure and Regulation of Protein Phosphatases", Annu. Rev. Biochem., vol. 58, pp. 453–508 (1989).

*Primary Examiner*—Lila Feisee
*Assistant Examiner*—Nirmal S. Basi
*Attorney, Agent, or Firm*—Elizabeth J. Hecht; William T. King; Ratner & Prestia

[57] ABSTRACT

Human PPP1R5 polypeptides and DNA (RNA) encoding such PPP1R5 and a procedure for producing such polypeptides by recombinant techniques is disclosed. Also disclosed are methods for utilizing such PPP1R5, or compounds which inhibit or stimulate PPP1R5 for dysfunctions or diseases which involve resistance to the action of insulin on glycogen synthesis are also disclosed. Agonist and antagonists of these PPP1R5 proteins and methods of their use are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding the PPP1R5 and for detecting altered levels of the polypeptide in a host.

21 Claims, 5 Drawing Sheets

CACGAGGCCG CGGGGGCAAG GCCTGGAGCT GTGGTTCGAA TTTGTGCAGG                50

CAGCGGGTGC TGGCTTTTAG GGTCCGCCGC CTCTCTGCCT A ATG AGC TGC            100
                                             Met Ser Cys
                                              1

ACC AGA ATG ATC CAG GTT TTA GAT CCA CGT CCT TTG ACA AGT TCG          145
Thr Arg Met Ile Gln Val Leu Asp Pro Arg Pro Leu Thr Ser Ser
     5               10                  15

GTC ATG CCC GTG GAT GTG GCC ATG AGG CTT TGC TTG GCA CAT TCA          190
Val Met Pro Val Asp Val Ala Met Arg Leu Cys Leu Ala His Ser
     20              25                  30

CCA CCT GTG AAG AGT TTC CTG GGC CCG TAC GAT GAA TTT CAA CGA          235
Pro Pro Val Lys Ser Phe Leu Gly Pro Tyr Asp Glu Phe Gln Arg
     35              40                  45

CGA CAT TTT GTG AAT AAA TTA AAG CCC CTG AAA TCA TGT CTC AAT          280
Arg His Phe Val Asn Lys Leu Lys Pro Leu Lys Ser Cys Leu Asn
     50              55                  60

ATA AAA CAC AAA GCC AAA TCA CAG AAT GAC TGG AAG TGC TCA CAC          325
Ile Lys His Lys Ala Lys Ser Gln Asn Asp Trp Lys Cys Ser His
     65              70                  75

AAC CAA GCC AAG AAG CGC GTT GTG TTT GCT GAC TCC AAG GGC CTC          370
Asn Gln Ala Lys Lys Arg Val Val Phe Ala Asp Ser Lys Gly Leu
     80              85                  90

TCT CTC ACT GCG ATC CAT GTC TTC TCC GAC CTC CCA GAA GAA CCA          415
Ser Leu Thr Ala Ile His Val Phe Ser Asp Leu Pro Glu Glu Pro
     95              100                 105

GCG TGG GAT CTG CAG TTT GAT CTC TTG GAC CTT AAT GAT ATC TCC          460
Ala Trp Asp Leu Gln Phe Asp Leu Leu Asp Leu Asn Asp Ile Ser
     110             115                 120

TCT GCC TTA AAA CAC CAC GAG GAG AAA AAC TTG ATT TTA GAT TTC          505
Ser Ala Leu Lys His His Glu Glu Lys Asn Leu Ile Leu Asp Phe
     125             130                 135

CCT CAA CCT TCA ACC GAT TAC TTA AGT TTC CGG AGC CAC TTT CAG          550
Pro Gln Pro Ser Thr Asp Tyr Leu Ser Phe Arg Ser His Phe Gln
     140             145                 150

AAG AAC TTT GTC TGT CTG GAG AAC TGC TCA TTG CAA GAG CGA ACA          595
Lys Asn Phe Val Cys Leu Glu Asn Cys Ser Leu Gln Glu Arg Thr
     155             160                 165

GTG ACA GGG ACT GTT AAA GTC AAA AAT GTG AGT TTT GAG AAG AAA          640
Val Thr Gly Thr Val Lys Val Lys Asn Val Ser Phe Glu Lys Lys
     170             175                 180

FIG. 1A

```
GTT CAG ATC CGT ATC ACT TTC GAT TCT TGG AAA AAC TAC ACT GAC   685
Val Gln Ile Arg Ile Thr Phe Asp Ser Trp Lys Asn Tyr Thr Asp
    185             190             195

GTA GAC TGT GTC TAT ATG AAA AAT GTG TAT GGT GGC ACA GAT AGT   730
Val Asp Cys Val Tyr Met Lys Asn Val Tyr Gly Gly Thr Asp Ser
    200             205             210

GAT ACC TTC TCA TTT GCC ATT GAC TTA CCC CCT GTC ATT CCA ACT   775
Asp Thr Phe Ser Phe Ala Ile Asp Leu Pro Pro Val Ile Pro Thr
    215             220             225

GAG CAG AAA ATT GAG TTC TGC ATT TCT TAC CAT GCT AAT GGG CAA   820
Glu Gln Lys Ile Glu Phe Cys Ile Ser Tyr His Ala Asn Gly Gln
    230             235             240

GTC TTT TGG GAC AAC AAT GAT GGT CAG AAT TAT AGA ATT GTT CAT   865
Val Phe Trp Asp Asn Asn Asp Gly Gln Asn Tyr Arg Ile Val His
    245             250             255

GTT CAA TGG AAG CCT GAT GGG GTG CAG ACA CAG ATG GCA CCC CAG   910
Val Gln Trp Lys Pro Asp Gly Val Gln Thr Gln Met Ala Pro Gln
    260             265             270

GAC TGT GCA TTC CAC CAG ACG TCT CCT AAG ACA GAG TTA GAG TCA   955
Asp Cys Ala Phe His Gln Thr Ser Pro Lys Thr Glu Leu Glu Ser
    275             280             285

ACA ATC TTT GGC AGT CCG AGG CTG GCT AGT GGG CTC TTC CCA GAG  1000
Thr Ile Phe Gly Ser Pro Arg Leu Ala Ser Gly Leu Phe Pro Glu
    290             295             300

TGG CAG AGC TGG GGG AGA ATG GAG AAC TTG GCC TCT TAT CGA       1042
Trp Gln Ser Trp Gly Arg Met Glu Asn Leu Ala Ser Tyr Arg
    305             310             315

GAATTAAGC AACAATGTAA CTGGTCTTGA CTTGTCATAT TCCCCCATGC         1092

AATCCTAGGT CTGTATTGCT CAATTTTAGG AAGCCTTTGC TACTCCATCA        1142

GTAGGTTTAG ATTTGA                                             1158
```

FIG. 1B

```
R5   MSCTRMIQVL  DPRPLTSSVM  PVDVAMRLCL  AHSPPVKSFL  GPYDEFQRRH    50
                      |  ||:           |           |
G_L                   M  AVDIEY----  -------SYS  SMAPSLRRER    20

R5   FVNKL-----  KPLKSCLNI-  -KHKAKSQND  WKCSHNQAKK  RVVFADSKGL    93
     |  |:       |||: |: :      |   |                ||  ||  |||  ||
G_L  FTFKISPKLN  KPLRPCIQLG  SKDEAGRMVA  PTVQEKKVKK  RVSFADNQGL    70

R5   SLTAIHVFSD  LPEEPAWDLQ  FDLLDLNDIS  SALKHHEEKN  LILDFPQPST   143
     ||  :  |||:      :     |:   |  :  ||       |           |       :|||||||
G_L  ALTMVKVFSE  F--DDPLDIP  FNITELLDNI  VSLTTAESES  FVLDFPQPSA   118

R5   DYLSFRSHFQ  KNFVCLENCS  LQERTVTGTV  KVKNVSFEKK  VQIRITFDSW   193
     |||  ||    |     |  ||||||||   |  |: :  |||     || |: |||    |  ||  |||:|
G_L  DYLDFRNRLQ  TNHVCLENCV  LKEKAIAGTV  KVQNLAFEKV  VKIRMTFDTW   168

R5   KNYTDVDCVY  MKNVYGGTDS  DTFSFAIDLP  PVIPTEQKIE  FCISYHANGQ   243
     |  :||    ||      |  |:|:|   ||||| |  ||    |:    :  |    :  |   |||
G_L  KSFTDFPCQY  VKDTYAGSDR  DTFSFDISLP  EKIQSYERME  FAVCYECNGQ   218

R5   VFWDNNDGQN  YRIVHVQWKP  DGVQTQMAPQ  DCAFHQTSPK  TELESTIFGS   293
     :||  |  |  |  |||    :           |          |   :   |||
G_L  SYWDSNKGKN  YRITRAELRS  TQGMTE----  ----PYNGPD  FGISFDQFGS   260

R5   PRLASGLFPE  WQSWGRMENL  ASYR                                 317
     ||   |||||  ||     |  :  |
G_L  PRCSFGLFPE  WPSYLGYEKL  GPYY                                 284
```

FIG. 2

| | | | |
|---|---|---|---|
| R5 | 157 | VCLE---NCSLQERTVTGTVKVKNVSFEKKVQIRI--TFDSWKNYT | 197 |
| G$_L$ | 132 | VCLE---NCVLKEKAIAGTVKVQNLAFEKVVKIRM--TFDTWKSFT | 172 |
| G$_M$ | 128 | AILES-TESLLGSTSIKGIIRVLNVSFEKLVYVRM--SLDDWQTHY | 170 |
| GAC1 | 244 | VKLHSLTQLGDDSSKITGLVYVKNLSFEKYLEIKF--TFNSWRDIH | 287 |
| AMYL | 33 | VQLDS---YNYDGSTFSGKIYVKNIAYSKKVTVIYADGSDNWNNNG | 75 |
| | | | |
| R5 | 198 | DVDCVYMKNVYGGTDSDTFSFAIDLPPVIPTEQ------------- | 230 |
| G$_L$ | 173 | DFPCQYVKDTYAGSDRDTFSFDISLPEKIQSYE------------- | 205 |
| G$_M$ | 171 | DILAEYVPNSCDG-ETDQFSFKIVLVPPYQKDGS------------ | 203 |
| GAC1 | 288 | YVTANFNRTIN--SNVDEFKFTIDLNSLKYILLIKRIITMEKNTSS | 331 |
| AMYL | 76 | NTIAASYSAPISGSNYEYWTFSASINGIK----------------- | 104 |
| | | | |
| R5 | 231 | ---KIEFCISYHANGQVFWDNNDGQNYRI | 256 |
| G$_L$ | 206 | ---RMEFAVCYECNGQSYWDSNKGKNYRI | 231 |
| G$_M$ | 204 | ---KVEFCIRYETSVGTFWSNNNGTNYTF | 229 |
| GAC1 | 332 | CPLNIELCCRYDVNNETYYDNNNGKNYHL | 360 |
| AMYL | 105 | -----EFYIKYEVSGKTYYDNNNSANYQV | 128 |

PROTEIN PHOSPHATASE 1 BINDING PROTEIN, R5

FIELD OF THE INVENTION

This invention relates generally to newly identified polypeptides and polynucleotides, variants and derivatives of the polynucleotides and polypeptides; polypeptides encoded by such polynucleotides, the use of such polynucleotides and polypeptides, as well as the production of such polynucleotides and polypeptides. In particular, the invention relates to novel polypeptides and polynucleotides related to a novel human protein related to the liver- and muscle-specific glycogen binding subunits of protein phosphatase 1. The novel protein is hereinafter called protein phosphatase 1 binding protein R5 or PPP1R5.

BACKGROUND OF THE INVENTION

Protein phosphatase 1 (PP1) participates in the regulation of a wide variety of cellular functions by reversible protein phosphorylation and is one of the major protein phosphatases dephosphorylating serine and threonine residues in eukaryotes. The ability of PP1 to regulate diverse functions resides in the capacity of PP1 to interact with a variety of regulatory subunits that may target PP1 to specific subcellular locations, modulate its substrate specificity, and allow its activity to be responsive to extracellular signals [Hubbard and Cohen, Trends Biochem. Sci.. 18:172–177 (1993)].

A 126 kDa glycogen binding subunit ($G_M$ or PPP1R3) targets PP1 to glycogen particles and to the sarcoplasmic reticulum in striated muscle [Tang et al., J. Biol. Chem. 266: 15782–15789 (1991); Chen et al., Diabetes, 43:1234–1241 (1994)]. The hormones insulin and adrenalin are thought to influence the activity of PP1 via the $G_M$ subunit. Phosphorylation of Ser-46 in human $G_M$, in response to insulin, enhances the rate at which at which PP1 dephosphorylates and activates glycogen synthase, causing an increase in glycogen synthesis [P. Dent et al, Nature, 348:302–308 (1990)]. In contrast, phosphorylation of Ser-65 in human $G_M$ by protein kinase A in response to B-adrenergic agonists triggers dissociation of PP1 from $G_M$, thus inhibiting PP1 from acting on glycogen synthase and phosphorylase and resulting in decreased glycogen synthesis and stimulation of glycogenolysis [Nakielny et al., Eur. J. Biochem., 199: 713–722 (1991)].

A distinct 33 kDa glycogen binding subunit ($G_L$ or PPP1R4), which is only 23% identical to the N-terminal portion of $G_M$, targets PP1 to glycogen in liver [Moorhead et al., FEBS Lett., 362:101–105 (1994); Doherty et al., FEBS Lett., 375:284–289 (1995)]. The binding of $G_L$ modulates the activity of PP1, enhancing the rate at which it dephosphorylates and activates glycogen synthase and suppressing the rate at which it inactivates phosphorylase. Hormonal regulation of the activity of PP1 in liver is not known to occur through the phosphorylation of $G_L$. Instead, the hormone glucagon (acting via cyclic AMP and protein kinase A) and a-adrenergic agonists (acting via $Ca^{+2}$) increase the levels of phosphorylase a, which to binds $G_L$ and potently inhibits PP1 at nanomolar concentrations. This inhibition is thought to be allosteric, since the $K_m$ for phosphorylase as a substrate of PP1 is in the micromolar range. Insulin acts by lowering the level of cyclic AMP in liver, thereby decreasing the level of phosphorylase a and relieving the inhibition of PP1-$G_L$ complex. Glycogen synthesis in liver is also stimulated by glucose, which binds to phosphorylase a, increasing the rate at which it is dephosphorylated.

Several other targeting subunits of PP1 have now been identified in mammals and these include the myosin binding targeting complex (comprising an $M_{110}$ and $M_{21}$ subunit) of smooth muscle, which enhances the dephosphorylation of myosin light chains by PP1 and is involved in the relaxation of smooth muscle [D. Alessi et al, Eur. J. Biochem.. 210:1023–1035 (1992); Y. H. Chen et al, FEBS Lett. 356:51–55 (1994)]. A distinct myosin targetting subunit of PP1 is present in striated muscles [P. Dent et al, Eur. J. Biochem., 210:1037–1044 (1992)]. A p53 binding protein (53BP2) [N. R. Helps et al, FEBS Lett., 377: 295–300 (1995)], a nuclear protein NIPP-1 [A. Van Eynde et al., J. Biol. Chem. 270:28068–28074 (1995)] and an RNA splicing factor PSF1 [K. Hirano et al, FEBS Lett., 389:191–194 (1996)] have been shown to bind to PP1. The retinoblastoma gene product [T. Durphee et al., Genes Dev. 7:555–569 (1993)], ribosomal proteins L5 [K. Hirano et al., J. Biol. Chem. 270:19786–19790 (1995)] and RIPP-1 [Buellens et al, Eur. J. Biochem., 239:183–189 (1996)] and a 110 kDa nuclear protein yet to be identified [I. Jagiello et al, J. Biol. Chem., 270:17257–17263 (1995)] are also reported to interact with PP1. The small cytosolic proteins, inhibitor-1, inhibitor-2 and DARPP-32 inhibit PP1 [P. Cohen, Annu. Rev. Biochem., 58:453–508 (1989)]. A complex between inhibitor-2 and PP1 has been isolated. More recently, inhibitor-2 has been shown to act like a molecular chaperon to fold PP1 into its native conformation [D. R. Alessi et al, Eur. J. Biochem., 213:1055–1066 (1993); C. MacKintosh et al, FEBS. Lett., (1996) in press]. A number of distinct PP1 targeting subunits have also been identified in yeast [M. J. R. Stark, Yeast (1996) in press].

Sites on the glycogen and myofibrillar targeting subunits which bind to PP1 have been localized [D. F. Johnson et al., Eur. J. Biochem., 239:317–325 (1996)] and a 13 residue peptide containing a RVXF motif common to many of the PP1 binding subunits has been crystallized as a complex with PP1 [M. Egloffet al., EMBO J. (1997) submitted].

Known PP1 subunits play a role in the regulation of glycogen metabolism and thus novel PP1 subunit proteins, agonists or antagonists thereof are anticipated to be beneficial in many diseases which involve resistance to the action of insulin on glycogen synthesis. Such disorders include, without limitation, diabetes mellitus, obesity, essential hypertension, dyslipidaemia and premature atherosclerosis, among others.

There, thus, exists a need in the art for a variety of PP1 binding proteins, antagonists and agonists thereof, as well as compositions and methods for the use of same.

SUMMARY OF THE INVENTION

In one aspect, the present invention provides polypeptides, inter alia, that have been identified as novel PP1 binding subunit polypeptides of human origin, as well as biologically active and diagnostically or therapeutically useful fragments, variants, analogs and derivatives thereof, variants and derivatives of the fragments, and analogs of the foregoing. These polypeptides have been identified as PP1 binding subunit polypeptides, e.g., by homology between the amino acid sequence set out in FIGS. 1A–1B and known amino acid sequences of other proteins such as $G_M$ and $G_L$ (see FIG. 4). In one embodiment, the present invention provides a novel human PP1 binding subunit which contains the PP1 binding motif, modulates the specificity of PP1 and is related to $G_L$, but has a much wider tissue distribution. This binding subunit is referred to as PPP1R5in accordance with the human genome nomenclature [P. T. W. Cohen, Adv. Prot. Phosphatases, 8:371–376 (1996)].

In another aspect of the present invention, there are provided non-naturally occurring synthetic, isolated and/or recombinant PPP1R5 polypeptides, fragments, consensus fragments and/or sequences having conservative amino acid substitutions of the PPP1R5 of the present invention. These polypeptides may bind PP1, or may also modulate, quantitatively or qualitatively, PPP1R5 ligand binding.

In another aspect, the present invention provides synthetic, isolated or recombinant polypeptides which are designed to inhibit or mimic various PPP1R5 proteins or fragments thereof.

In another aspect of the invention, there are provided isolated nucleic acid molecules encoding PPP1R5 polypeptides, particularly human PPP1R5. Such molecules include polynucleotides, mRNAs, DNAs, cDNAs, genomic DNAs and fragments thereof, as well as analogs and biologically active and diagnostically or therapeutically useful variants, analogs or derivatives thereof, including fragments of the variants, analogs and derivatives.

In a particularly preferred embodiment of this aspect of the invention, the polynucleotide comprises the region encoding human PPP1R5 in the sequence set out in FIGS. 1A–1B [SEQ ID NOS: 1 and 2]. Among the particularly preferred embodiments of this aspect of the invention are naturally occurring allelic variants of human PPP1R5.

In yet another aspect of the present invention, there is provided an isolated nucleic acid molecule encoding a mature polypeptide expressible from the human cDNA contained in plasmid pHGBDX21.

In still another aspect, this invention provides nucleic acid probes comprising nucleic acid molecules of sufficient length to specifically hybridize to nucleic acid sequences of the present invention, e.g., human PPP1R5 sequences.

In another aspect, the invention provides a process for producing the aforementioned polypeptides, polypeptide fragments, variants and derivatives, fragments of the variants and derivatives, and analogs of the foregoing. In a preferred embodiment, the invention provides methods for producing the aforementioned PPP1R5 polypeptides by recombinant techniques comprising culturing recombinant prokaryotic and/or eukaryotic host cells, containing (i.e., having expressibly incorporated therein) a nucleic acid sequence encoding a polypeptide of the present invention under conditions permitting expression of human PPP1R5 polypeptide in the host and then recovering the expressed polypeptide.

In still another aspect, the invention provides products, compositions, processes and methods that utilize the aforementioned polypeptides and polynucleotides for research, biological, clinical and therapeutic purposes, inter alia. PPP1R5 polypeptides, particularly human PPP1R5 polypeptides, may be employed for therapeutic purposes, including, but not limited to, treatments of many diseases which involve resistance to the action of insulin on glycogen synthesis. Such disorders include, without limitation, diabetes mellitus, obesity, essential hypertension, dyslipidaemia and premature atherosclerosis, among others.

Also provided are compositions and methods that can be useful as potential modulators of PPP1R5 function, by binding to PP1, other ligands, and/or modulating ligand binding, and which due to their expected biological properties may be used in diagnostic, therapeutic and/or research applications.

In another aspect, the invention provides a method for utilizing these polypeptides and proteins for the screening of chemical or natural compounds or ligands thereof which inhibit or stimulate the interaction of the PPP1R5 polypeptides with PP1, inhibit or stimulate their interaction with other proteins, inhibit or stimulate the translocation of these polypeptides to the nucleus, and inhibit or stimulate the interaction of these polypeptides with nucleic acid sequences.

In accordance with certain preferred embodiments of this aspect of the invention, there are provided products, compositions and methods, inter alia, for, among other things, assessing PPP1R5 expression in cells by determining PPP1R5 polypeptides or PPP1R5-encoding mRNA; treating dysfunctions or diseases including, but not limited to, those identified above, in vitro, ex vivo or in vivo by exposing cells to PPP1R5 polypeptides or polynucleotides as disclosed herein; assaying genetic variation and aberrations, such as defects, in PPP1R5 genes; and administering a PPP1R5 polypeptide to an organism to augment PPP1R5 function or remediate PPP1R5 dysfunction.

In yet another aspect of the present invention, there is provided a process of using such activating compounds to stimulate the polypeptides of the present invention for the treatment of conditions related to the under-expression of PPP1R5.

In still a further aspect of the present invention, there is provided a process of using such inhibiting compounds for treating conditions associated with over-expression of PPP1R5.

In another aspect of the invention, there are provided antibodies against PPP1R5 polypeptides, including humanized antibodies, anti-antibodies, monoclonal and polyclonal antibodies. In certain particularly preferred embodiments in this regard, the antibodies are highly selective for human PPP1R5.

In yet a further aspect, the present invention provides agonists to the polypeptides of the present invention. Agonists to the polypeptides of the present invention can be used in the treatment of many diseases which involve resistance to the action of insulin on glycogen synthesis. Such disorders include, without limitation, diabetes mellitus, obesity, essential hypertension, dyslipidaemia and premature atherosclerosis, among others. Among preferred agonists are molecules that mimic PPP1R5, that bind to PP1, or other PPP1R5-binding molecules or receptor molecules, and that elicit or augment PPP1R5-induced responses. Also among preferred agonists are molecules that interact with PPP1R5, or PPP1R5 polypeptides, or with other modulators of PPP1R5 activities, and thereby potentiate or augment an effect of PPP1R5 or more than one effect of PPP1R5.

In another aspect of the present invention, there are provided PPP1R5 antagonists, which can be targeted against the binding of PPP1R5 with PP1, translocation, modification of other downstream proteins, and interaction with cis elements. Antagonists of PPP1R5 activity can be used in the treatment of the diseases identified above. Among preferred antagonists are those which mimic PPP1R5 so as to bind to PP1 or other binding molecules but not elicit a PPP1R5-induced response or more than one PPP1R5-induced response. Also among preferred antagonists are molecules that bind to or interact with PPP1R5 so as to inhibit an effect of PPP1R5 or more than one effect of PPP1R5 or which prevent expression of PPP1R5.

In a further aspect of the invention, there are provided compositions comprising a PPP1R5 polynucleotide or a PPP1R5polypeptide for administration to cells in vitro, to cells ex vivo and to cells in vivo, or to a multicellular organism. In certain particularly preferred embodiments of this aspect of the invention, the compositions comprise a PPP1R5 polynucleotide for expression of a PPP1R5 polypeptide in a host organism for treatment of disease. Particularly preferred in this regard is expression in a human patient for treatment of a dysfunction associated with aberrant endogenous activity of PPP1R5.

In still another aspect, the present invention provides diagnostic assays for detecting diseases related to overexpression of the polypeptides of the present invention and mutations in the nucleic acid sequences encoding such polypeptide. For example, the sequence of PPP1R5 can be used in diagnostics for the detection of overexpression which would be useful in detection of various diseases, including those identified above.

Another aspect of this invention provides a process for utilizing these sequences in the detection of mutations of these PPP1R5 polypeptides as indicators of several of the diseases mentioned above, among others.

A further aspect of the present invention provides a process for utilizing such polypeptides, or polynucleotides encoding such polypeptides, for in vitro purposes related to scientific research, synthesis of DNA and manufacture of DNA vectors.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

FIGS. 1A and 1B illustrate the complementary DNA (cDNA) and predicted protein sequences [SEQ ID NOS: 1 and 2] of the human protein phosphatase 1 binding subunit R5 (PPP1R5). Several protein sequences for PPP1R5 may be selected from SEQ ID NO: 2, if the initiating Met codon is at amino acids 1, 6, 20 or 26 of the sequence.

FIG. 2 illustrates a comparison of the amino acid sequence of PPP1R5 [SEQ ID NO: 2] with the glycogen binding subunit ($G_L$) of protein phosphatase 1 from rat liver [SEQ ID NO: 3]. Identities are shown by vertical lines. Conservative amino acid changes are indicated by colons in the following groups (L,I,V); (A,G); (S,T); (D, E); (Q,N); (R,K); (F,Y). Residues that are identical in R5, $G_L$ and the glycogen binding subunit ($G_M$) of human protein phosphatase 1 are underlined. The minimal PP1 binding motif is double underlined.

FIG. 4 compares the sequences of PPP1R5 [SEQ ID NO: 2], rat $G_L$ [SEQ ID NO: 3], human $G_M$ [SEQ ID NO: 4], *S. cerevisiae* GAC1 [SEQ ID NO: 5] and *Rhizopus oryzae* glucoamylase (AMYL) [SEQ ID NO: 6]. Amino acids that are conserved in all five proteins are underlined and those that are identical are double underlined.

GLOSSARY

Figure 3:
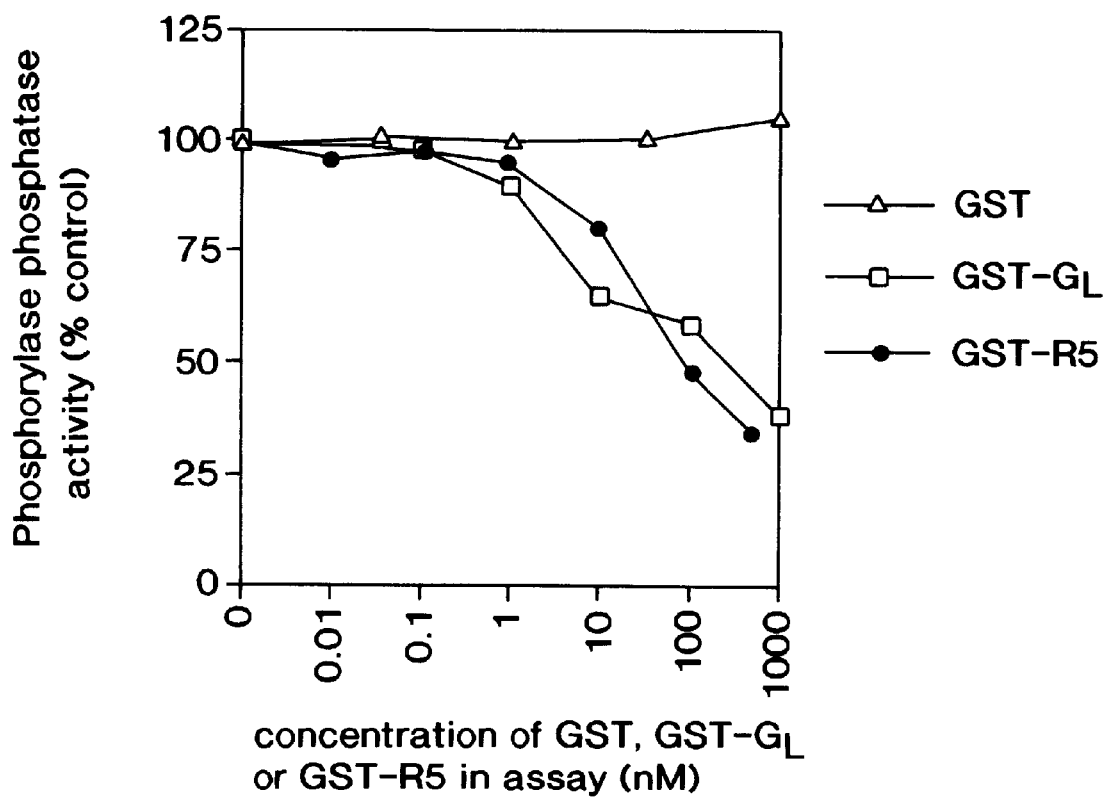
FIG. 3 is a graph depicting the comparison of the effects of the glutathione-S-transferase (GST)-R5 fusion protein and GST-$G_L$ fusion protein on the phosphorylase phosphatase activity of protein phosphatase 1. The phosphorylase phosphatase activities of PP1 in the presence of GST-R5 (open squares) and GST-$G_L$ (filled circles) and GST (open triangles) are shown. Activities are presented as a percentage of the initial PP1 activity.

The following illustrative explanations are provided to facilitate understanding of certain terms used frequently herein, particularly in the examples. The explanations are provided as a convenience and are not meant to limit the invention.

The term "gene" means the segment of DNA involved in producing a polypeptide chain; it includes regions preceding and following the coding region (leader and trailer) as well as intervening sequences (introns) between individual coding segments (exons).

"Digestion" of DNA refers to catalytic cleavage of a DNA with an enzyme, such as, but not limited to, a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 microgram of plasmid or DNA fragment is digested with about 2 units of enzyme in about 20 microliter of reaction buffer. For the purpose of isolating DNA fragments for plasmid construction, typically 5 to 50 micrograms of DNA are digested with 20 to 250 units of enzyme in proportionately larger volumes. Appropriate buffers and substrate amounts for particular restriction enzymes are described in standard laboratory manuals, such as those referenced below, and they are specified by commercial suppliers. Incubation times of about 1 hour at 37° C. are ordinarily used, but conditions may vary in accordance with standard procedures, the supplier's instructions, and the particulars of the reaction. After digestion, reactions may be analyzed, and fragments may be purified by electrophoresis through an agarose or polyacrylamide gel, using well known methods that are routine for those skilled in the art to isolate the desired fragment.

"Genetic element" generally means a polynucleotide comprising a region that encodes a polypeptide or a region that regulates replication, transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome, not in their natural state but, rather, following manipulation such as isolation, cloning and introduction into a host cell in the form of purified DNA or in a vector, among others.

"Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. With respect to polynucleotides, the term "isolated" means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, because they would not be in their naturally occurring form or environment. Similarly, the polynucleotides and polypeptides may occur in a composition, such as media, formulations, solutions for introduction of polynucleotides or polypeptides (for example, into cells), compositions or solutions for chemical or enzymatic reactions, for instance, which are not naturally occurring compositions, and, therein remain isolated polynucleotides or polypeptides within the meaning of that term as it is employed herein.

"Ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. 1989, hereinafter referred to as "Sambrook et al".

"Oligonucleotide(s)" refers to relatively short polynucleotides. Often the term refers to single-stranded deoxyribonucleotides, but it can refer as well to single-or double-stranded ribonucleotides, RNA:DNA hybrids and double-stranded DNAs, among others. Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, will readily form a ATG50033 phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

"Plasmids" are genetic elements that are stably inherited without being a part of the chromosome of their host cell. They may be comprised of DNA or RNA and may be linear or circular. Plasmids code for molecules that ensure their replication and stable inheritance during cell replication and may encode products of considerable medical, agricultural and environmental importance. For example, they code for toxins that greatly increase the virulence of pathogenic bacteria. They can also encode genes that confer resistance to antibiotics. Plasmids are widely used in molecular biology as vectors used to clone and express recombinant genes. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures.

Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

"Polynucleotide(s)" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are polynucleotides as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide, as it is employed herein, embraces such chemically, enzymatically or metabolically modified forms of polynucleotides, as well as the chemical forms of DNA and RNA characteristic of viruses and cells, including inter alia simple and complex cells.

"Polypeptides", as used herein, includes all polypeptides as described below. The basic structure of polypeptides is well known and has been described in innumerable textbooks and other publications in the art. The term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, or by chemical modification techniques which are well known to the art. The numerous common modifications that occur naturally in polypeptides are well described in basic texts and in more detailed monographs, as well as in a voluminous research literature, and are well known to those of skill in the art.

Among the known modifications which may be present in polypeptides of the present invention are, without limitation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, PROTEINS—STRUCTURE AND MOLECULAR PROPERTIES, 2nd Ed., T. E. Creighton, W. H. Freeman and Company, New York, 1993. Many detailed reviews are available on this subject, such as those provided by Wold, F., "Posttranslational Protein Modifications: Perspectives and Prospects", pgs. 1–12 in POSTTRANSLATIONAL COVALENT MODIFICATION OF PROTEINS, B. C. Johnson, Ed., Academic Press, New York, 1983; Seifter et al., *Meth. Enzymol.* 182:626–646 (1990), and Rattan et al., *Ann. N.Y. Acad. Sci.*, 663:48–62 (1992).

It is well known in the art that polypeptides are not always entirely linear. For instance, polypeptides may be branched as a result of ubiquitination, and they may be circular, with or without branching, generally as a result of posttranslational events, including natural processing events and events brought about by human manipulation which do not occur naturally. Circular, branched and branched circular polypeptides may be synthesized by non-translation natural processes and by entirely synthetic methods, as well.

Modifications can occur anywhere in a polypeptide, including the peptide backbone, the amino acid side-chains and the amino or carboxyl termini In fact, blockage of the amino or carboxyl group in a polypeptide, or both, by a covalent modification, is common in naturally occurring and synthetic polypeptides and such modifications may be present in polypeptides of the present invention. For instance, the amino terminal residue of polypeptides made in *E. coli*, prior to processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having the native patterns of glycosylation, inter alia. Similar considerations apply to other modifications.

It will be appreciated that the same type of modification may be present in the same or varying degrees at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

Variants include a polynucleotide that differs in nucleotide sequence from another, reference polynucleotide. Generally, differences are limited so that the nucleotide sequences of the reference and the variant are closely similar overall and, in many regions, are identical.

As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

Variants include a polypeptide that differs in amino acid sequence from another, reference polypeptide. Generally, differences are limited so that the sequences of the reference and the variant are closely similar overall and, in many regions, are identical.

A variant and reference polypeptide may differ in amino acid sequence by one or more substitutions, additions, deletions, fusions and truncations, which may be present in any combination.

"Fusion protein" as the term is used herein, is a protein encoded by two, often unrelated, fused genes or fragments thereof European Patent Application No. EP-A-O 464 533 [Canadian counterpart Patent Application No. 2045869] discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [See, e.g., European Patent Application No. EP-A 0232 262]. For some uses, it would be desirable to be able to delete the Fc part after the fusion protein has been expressed, detected and purified. Accordingly, it may be desirable to link the two components of the fusion protein with a chemically or enymatically cleavable linking region. This is the case when the Fc portion proves to be a hindrance to use in therapy and diagnosis, for example, when the fusion protein is to be used as an antigen for immunizations. In drug discovery, for example, human proteins, such as hIL-5, have been fused with Fc portions for use in high-throughput screening assays to identify antagonists of hIL-5. See, D. Bennett et al., *J. Mol. Recog.*, 8:52–58 (1995); and K. Johanson et al., *J. Biol. Chem.*, 270(16):9459–9471 (1995).

Thus, this invention also relates to genetically engineered soluble fusion proteins comprised of PPP1R5 or a portion thereof, and of various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for diagnosis and therapy. A further aspect of the invention also relates to polynucleotides encoding such fusion proteins.

Membrane-bound receptors are particularly useful in the formation of fusion proteins. Such receptors are generally characterized as possessing three distinct structural regions: an extracellular domain, a transmembrane domain and a cytoplasmic domain. This invention contemplates the use of one or more of these regions as components of a fusion protein. Examples of such fusion protein technology can be found in International Patent Application Nos. WO94/29458 and WO94/22914.

"Binding molecules" (or otherwise called "interaction molecules" or "receptor component factors") refer to molecules, including ligands, that specifically bind to or interact with polypeptides of the present invention. For example, PP1 is a known binding molecule. Such binding molecules are a part of the present invention. Binding molecules may also be non-naturally occurring, such as antibodies and antibody-derived reagents that bind specifically to polypeptides of the invention.

As known in the art, "similarity" between two polypeptides is determined by comparing the amino acid sequence and its conserved amino acid substitutes of one polypeptide to the sequence of a second polypeptide. Moreover, also known in the art is "identity" which means the degree of sequence relatedness between two polypeptide or two polynucleotide sequences as determined by the identity of the match between two lengths of such sequences. Both identity and similarity can be readily calculated [COMPUTATIONAL MOLECULAR BIOLOGY, Lesk, A. M., ed., Oxford University Press, New York, (1988); BIOCOMPUTING: INFORMATICS AND GENOME PROJECTS, Smith, D. W., ed., Academic Press, New York, (1993); COMPUTER ANALYSIS OF SEQUENCE DATA, PART I, Griffin, A. M., and Griffin, H. G., eds., Humana Press, New Jersey, (1994); SEQUENCE ANALYSIS IN MOLECULAR BIOLOGY, von Heinje, G., Academic Press, (1987); and SEQUENCE ANALYSIS PRIMER, Gribskov, M. and Devereux, J., eds., M Stockton Press, New York, (1991)]. A number of methods exist to measure identity and similarity between two polynucleotide or polypeptide sequences. The terms "identity" and "similarity" are well known to skilled artisans [H. Carillo and D. Lipton, *SIAM J. Applied Math.* 48:1073 (1988)]. Methods commonly employed to determine identity or similarity between two sequences include, but are not limited to, those disclosed in Guide to Huge Computers, Martin J. Bishop, ed., Academic Press,. San Diego, 1994, and H. Carillo and D. Lipton, *SIAM J. Applied Math.*, 48:1073 (1988). Preferred methods to determine identity are designed to give the largest match between the two sequences tested. Methods to determine identity and similarity are codified in computer programs. Preferred computer program methods to determine identity and similarity between two sequences include, but are not limited to, GCS program package [J. Devereux et al., *Nucl. Acids Res.,* 12(1):387 (1984)], BLAST, FASTA [S. F. Atschul et al., *J. Mol. Biol.,* 215:403 (1990)].

DETAILED DESCRIPTION OF THE INVENTION

The present invention relates to novel polypeptides putatively identified as human PP1 binding subunit PPP1R5 polypeptides, and polynucleotides encoding same. This identification has been made as a result of amino acid sequence homology of PPP1R5 to other PP1 binding proteins. The human protein PPP1R5 identified here is most closely related to the rat liver glycogen binding subunit ($G_L$) of PP1, i.e., by 42% amino acid identity. PPP1R5 has a 28% identity to the N-terminal region of the glycogen binding subunit $G_M$ of PP1 from human skeletal muscle.

The invention relates especially to PPP1R5, a full length clone which covers the putative coding region of a PP1 binding protein based on the above homologies and on other characteristics discussed below. PPP1R5 has nucleotide and amino acid sequences [SEQ ID NOS: 1 and 2, respectively] set out in FIGS. 1A–1B. See also Example 1.

PPP1R5's fairly low sequence identity to $G_L$ and much wider tissue distribution (see Examples below) indicate that it is unlikely to be the human homolog of $G_L$. PPP1R5 also differs from $G_L$ in that it does not bind phosphorylase a, which is known to regulate the activity of the PP1-$G_L$ complex. Coprecipitation studies demonstrated that PPP1R5 will form a complex with PP1 and inspection of the sequence of PPP1R5 show that it possesses the RVXF motif (double underlined in FIG. 2), which is involved in the binding of $G_M$ and $G_L$ to PP1 [D. F. Johnson et al, (1996), cited above] and is common to a number of other PP1 binding proteins. PPP1R5 therefore represents a novel PP1 binding protein.

PPP1R5 and $G_L$ show similar inhibition of phosphorylase phosphatase activity. Therefore, like other regulatory subunits of PP1, PPP1R5 may modulate the specificity of PP1 towards particular substrates. The identification of cDNAs encoding PPP1R5 in a large number of different tissues including liver, indicates that unlike $G_L$ which is liver specific and $G_M$ which is found in muscles (skeletal, diaphragm and heart), PPP1R5 provides a function common to many tissues. The aggregation properties of PPP1R5 and $G_L$ cause PPP1R5 to pellet on centrifugation in both the presence and absence of glycogen. However, PPP1R5 does contain a region (amino acids 170–181 of SEQ ID NO: 2) homologous to a postulated glycogen binding site in $G_M$ [Hubbard and Cohen, (1993) cited above].

Interestingly an extensive region of PPP1R5 which does not contain the RVXF PP1 binding site, is conserved in *Rhizopus oryzae* glucoamylase, an enzyme which is secreted from the fungus and degrades starch [Y. Tanaka et al, *Agric. Biol. Chem.,* 50: 965–969 (1986)]. An alignment of PPP1R5 (amino acids 157 to 256 of SEQ ID NO: 2) with the sequences of $G_L$ [SEQ ID NO: 3], $G_M$ [SEQ ID NO: 4], *S. cerevisiae* GAC1 [J. M. Francois et al, *EMBO J.,* 11:87–96 (1992), SEQ ID NO: 5] and *R oryzae* glucoamylase (amino acids 33–129 of SEQ ID NO: 6) is shown in FIG. 4. Since amino acids 26–109 [SEQ ID NO: 6] of *R oryzae* glucoamylase have been shown to adsorb to raw starch [Tanaka, cited above], and $G_L$, $G_M$ and GAC1 all bind to glycogen, it seems likely that part of all of the sequence shown in FIG. 4 may be a carbohydrate binding domain. *S. cerevisiae* GIP2, a PP1 binding protein whose function is unknown, has also recently been shown to align to part of this region [J. Tu et al, *Molecular and Cellular Biology,* 16(8):4199–4206 (1996)]. PPP1R5 is likely to be involved in the regulation of glycogen metabolism in a wide ranges of tissues, besides liver and muscle. However, the hormonal regulation of PPP1R5 must differ from that of $G_M$ and $G_L$. Neither of the serine residues that are phosphorylated in $G_M$ in response to insulin and adrenalin are conserved in PPP1R5, nor is the phosphorylase a binding site which is involved in the allosteric regulation of $G_L$ by hormones. Like other regulatory subunits of PP1, PPP1R5 increases the specificity of PP1 towards particular substrates by modulating its activity.

Polynucleotides

The present invention provides an isolated nucleic acid (polynucleotide) which encodes the mature PPP1R5 polypeptide having the deduced amino acid sequence of FIGS. 1A–1B [SEQ ID NOS: 1 and 2].

Using the information provided herein, such as the polynucleotide sequence set out in FIGS. 1A–1B [SEQ ID NO: 1], a polynucleotide of the present invention encoding human PPP1R5 may be obtained using standard cloning and screening procedures. Illustrative of the invention, the polynucleotide set out in FIGS. 1A–1B [SEQ ID NO: 1] was discovered in a cDNA library derived from human gall bladder cells using the expressed sequence tag (EST) analysis [M. D. Adams et al., *Science,* 252:1651–1656 (1991); M. D. Adams et al., *Nature,* 355:632–634 (1992); M. D. Adams et al., *Nature.* 377 Supp:3–174 (1995)].

Human PPP1R5 of the invention is structurally related to other PP1 binding proteins. For example, the cDNA sequence of PPP1R5 [FIGS. 1A–1B and SEQ ID NO: 1] contains an open reading frame encoding a polypeptide of 317 amino acids, assuming translation starts at codon number 1. Alternative protein sequences span amino acids 6–317, 20–317, or 26–317, producing proteins of 312, 298 and 292 amino acids in length respectively, depending on the initiating Met. The amino acid sequence of human PPP1R5 shows 42% identity to rat liver $G_L$ and 51% similarity if conservative substitutions are taken into account (FIG. 2). PPP1R5 is less similar to $G_M$, showing only 27% and 28% identity to the first 285 amino acids of rabbit and human $G_M$, respectively. This sequence encodes a protein having a deduced molecular weight of between about 36 kDa to about 38kDa. See, e.g., FIGS. 2 and 4 and Example 1 below.

Polynucleotides of the present invention may be in the form of RNA, such as mRNA, or in the form of DNA, including, for instance, cDNA and genomic DNA obtained by cloning or synthetic DNA produced by chemical synthetic techniques or by a combination thereof The DNA may be double-stranded or single- stranded. Single-stranded DNA may be the coding strand, also known as the sense strand, or it may be the non-coding strand, also referred to as the anti-sense strand.

The sequence which encodes the mature polypeptide may be identical to the coding sequence of the polynucleotide shown in FIGS. 1A–1B [SEQ ID NO: 1]. It also may be a polynucleotide with a different coding sequence, which, as a result of the redundancy (degeneracy) of the genetic code, also encodes the same mature polypeptide of FIGS. 1A–1B [SEQ ID NO: 2].

Polynucleotides of the present invention which encode the polypeptide of FIGS. 1A–1B may include, but are not limited to, the coding sequence for the mature polypeptide, by itself; the coding sequence for the mature polypeptide and additional coding sequences, such as those encoding a leader or secretory sequence, such as a pre-, or pro- or prepro-protein sequence; and the coding sequence of the mature polypeptide, with or without the aforementioned additional coding sequences, together with additional, non-coding sequences, including, but not limited to, introns and non-coding 5' and 3' sequences, such as the transcribed, non-translated sequences that play a role in transcription, and mRNA processing, including splicing and polyadenylation signals, for example, for ribosome binding and stability of mRNA. Coding sequences which provide additional functionalities may also be incorporated into the polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for instance, the polypeptide may be fused in frame to a marker sequence, such as a peptide, which facilitates purification of the fused polypeptide. In certain preferred embodiments of this aspect of the invention, the marker sequence is a hexa-histidine peptide, such as the tag provided in the pQE-9 vector (Qiagen, Inc.) to provide for purification of the mature polypeptide fused to the marker in the case of a bacterial host. Alternatively, for example, as described in Gentz et al., *Proc. Natl. Acad. Sci.. USA* 86:821–824 (1989), hexa-histidine provides for convenient purification of the fusion protein. In other embodiments, the marker sequence is a hemagglutinin (HA) tag, particularly when a mammalian host, e.g. COS-7 cells, is used. The HA tag corresponds to an epitope derived from influenza hemagglutinin protein [see, e.g., Wilson et al., *Cell,* 37:767 (1984)]. Many other such tags are commercially available.

In accordance with the foregoing, the term "polynucleotide encoding a polypeptide" as used herein encompasses polynucleotides which include, by virtue of the redundancy of the genetic code, any sequence encoding a polypeptide of the present invention, particularly the human PPP1R5 having the amino acid sequence set out in FIGS. 1A–1B [SEQ ID NO: 2]. The term includes only coding sequence for the polypeptide as well as a polynucleotide which includes additional coding and/or non-coding sequence. The term also encompasses polynucleotides that include a single continuous region or discontinuous regions encoding the polypeptide (for example, interrupted by introns) together with additional regions, that also may contain coding and/or non-coding sequences.

The present invention further relates to variants of the herein above-described polynucleotides which encode for fragments, analogs and derivatives of the polypeptide having the deduced amino acid sequence of FIGS. 1A–1B (SEQ ID NOS: 2). A variant of the polynucleotide may be a naturally occurring variant of SEQ ID NOS: 1 and 2, such as a naturally occurring allelic variant, or it may be a variant that is not known to occur naturally. As known in the art, an allelic variant is an alternate form of a polynucleotide sequence which may have a substitution, deletion or addition of one or more nucleotides, which does not substantially alter the function of the encoded polypeptide. Non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of PPP1R5 as set out in FIGS. 1A–1B [SEQ ID NO: 2]; variants, analogs, derivatives and fragments thereof, and fragments of the variants, analogs and derivatives.

Further particularly preferred in this regard are polynucleotides encoding PPP1R5 variants, analogs, derivatives and fragments, and variants, analogs and derivatives of the fragments, which have the amino acid sequence of the PPP1R5 polypeptide of FIGS. 1A–1B. Such polypeptides include those in which several, a few, 5 to 10, 1 to 5, 1 to 3, 2, 1 or no amino acid residues are substituted, deleted or added, in any combination. Especially preferred among these are silent substitutions, additions, insertion and deletion variants, which do not alter the properties and activities of the PPP1R5. Also especially preferred in this regard are conservative substitutions. Most highly preferred are polynucleotides encoding polypeptides having the amino acid sequence of FIGS. 1A–1B, without substitutions.

Further preferred embodiments of the invention are polynucleotides that are at least about 70% identical to a polynucleotide encoding the PPP1R5 polypeptide having the amino acid sequence set out in FIGS. 1A–1B, and polynucleotides which are complementary to such polynucleotides. Most highly preferred are polynucleotides that comprise a region that is at least 75% identical to a polynucleotide encoding the PPP1R5 polypeptide and polynucleotides complementary thereto. In this regard, polynucleotides at least 90% identical to the same are particularly preferred, and those with at least 95% are especially preferred. Furthermore, those with at least 97% are highly preferred and those with at least 98–99% are most highly preferred, with at least 99% being the most preferred.

Particularly preferred embodiments in this respect, moreover, are polynucleotides which encode polypeptides which retain substantially the same biological function or activity as the mature polypeptide encoded by the cDNA of FIGS. 1A–1B.

The present invention further relates to polynucleotides that hybridize to the herein above-described sequences, particularly if there is at least 80% identity between the sequences as discussed above. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, polynucleotides of the invention, including PPP1R5 fragments, may be used as hybridization probes for cDNA and genomic DNA, to isolate full-length cDNAs and genomic clones encoding PPP1R5 and to isolate cDNA and genomic clones of other genes that have a high sequence similarity to the human PPP1R5 gene and/or similar biological activity. Such probes generally will comprise at least 15 nucleotides. Preferably, such probes will have at least 30 nucleotides and may have at least 50 nucleotides. Particularly preferred probes will range between 30 and 50 nucleotides. The probe may also be used to identify a cDNA clone corresponding to a full length transcript and a genomic clone or clones that contain the complete PPP1R5 gene including regulatory and promotor regions, exons, and introns.

An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The polynucleotides which hybridize to the hereinabove described polynucleotides in a preferred embodiment encode polypeptides which either retain substantially the same biological function or activity as the mature polypeptide encoded by the cDNA of FIGS. 1A–1B (SEQ ID NO:1).

For example, such polynucleotides may be employed as probes for the polynucleotide of SEQ ID NO: 1, for example, for recovery of the polynucleotide or as a diagnostic probe or as a PCR primer. For example, the coding region of the PPP1R5 gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine the members of the library to which the probe hybridizes.

The polynucleotides and polypeptides of the present invention may be employed as research reagents and materials for discovery of treatments and diagnostics to human disease, as further discussed herein relating to polynucleotide assays.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes. A precursor protein, having the mature form of the polypeptide fused to one or more prosequences, may be an inactive form of the polypeptide. When prosequences are removed, such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Polypeptides

The present invention relates to a human PPP1R5 polypeptide which has the deduced amino acid sequence of FIGS. 1A–1B [SEQ ID NO: 2]. The invention also relates to variants, analogs, derivatives and fragments of these polypeptides, and variants, analogs and derivatives of the fragments. The terms "fragment," "derivative" and "analog" when referring to the polypeptide of FIGS. 1A–1B, means a polypeptide which retains essentially the same biological function or activity as such polypeptide, i.e., functions as a PPP1R5, or retains the ability to bind PP1 or other binding molecules. Thus, an analog includes, for example, a proprotein which can be activated by cleavage of the proprotein portion to produce an active mature polypeptide. The polypeptide of the present invention may be a recombinant polypeptide, a natural polypeptide or a synthetic polypeptide. In certain preferred embodiments, it is a recombinant polypeptide.

The fragment, derivative or analog of the polypeptide of FIGS. 1A–1B or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of this invention are polypeptides having the amino acid sequence of human PPP1R5 set out in FIGS. 1A–1B as SEQ ID NO: 2, variants, analogs, derivatives and fragments thereof, and variants, analogs and derivatives of the fragments. Further particularly preferred embodiments of the invention in this regards are polypeptides having the amino acid sequence of human PPP1R5 set out in FIGS. 1A–1B as SEQ ID NO: 2, variants, analogs, derivatives and fragments thereof, and variants, analogs and derivatives of the fragments which retain the activity/function of this enzyme.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further particularly preferred in this regard are variants, analogs, derivatives and fragments, and variants, analogs and derivatives of the fragments, having the amino acid sequence of the PPP1R5 of FIGS. 1A–1B, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the PPP1R5. Also especially preferred in this regard are conservative substitutions. Most highly preferred are polypeptides having the amino acid sequence of FIGS. 1A–1B [SEQ ID NO: 2] without substitutions.

The polypeptides and polynucleotides of the present invention are preferably provided in an isolated form, and preferably are purified to homogeneity.

The polypeptides of the present invention include the polypeptide of SEQ ID NO: 2 (in particular the mature polypeptide) as well as polypeptides which have at least about 70% identity to the polypeptide of SEQ ID NO: 2 and more preferably at least 80% similarity (more preferably at least 80% identity) to the polypeptide of SEQ ID NO: 2 and still more preferably at least 90% similarity (still more preferably at least 90% identity) to the polypeptide of SEQ ID NO: 2 and also include portions of such polypeptides with such portion of the polypeptide generally containing at least 30 amino acids and more preferably at least 50 amino acids.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention. Fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a PPP1R5 polypeptide of the present comprised within a precursor polypeptide designed for expression in a host and having heterologous pre- and pro-polypeptide regions fused to the amino terminus of the PPP1R5 fragment and an additional region fused to the carboxyl terminus of the fragment. Therefore, fragments in one aspect of the meaning intended herein, refers to the portion or portions of a fusion polypeptide or fusion protein derived from PPP1R5.

As representative examples of polypeptide fragments of the invention, there may be mentioned those which have from about 5–15, 10–20, 15–40, 30–55, 41–75, 41–80, 41–90, 50–100, 75–100, 90–115, 100–125, and 110–113 amino acids in length. In this context "about" includes the particularly recited range and ranges larger or smaller by several, a few, 5, 4, 3, 2 or 1 amino acid residues at either extreme or at both extremes. For instance, about 40–90 amino acids in this context means a polypeptide fragment of 40 plus or minus several, a few, 5, 4, 3, 2 or 1 amino acid residues to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids. Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 5–15, 10–20, 15–40, 30–55, 41–75, 41–80, 41–90, 50–100, 75–100, 90–115, 100–125, and 110–113 amino acids long.

Among especially preferred fragments of the invention are truncation mutants of PPP1R5. Truncation mutants include PPP1R5 polypeptides having the amino acid sequence of FIGS. 1A–1B, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out above also are preferred embodiments of truncation fragments, which are especially preferred among fragments generally.

Also preferred in this aspect of the invention are fragments characterized by structural or functional attributes of PPP1R5. Preferred embodiments of the invention in this regard include fragments, if available, that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of PPP1R5. Among highly preferred fragments in this regard are those that comprise regions of PPP1R5 that combine several structural features, such as several of the features set out above. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of PPP1R5. Most highly preferred in this regard are fragments that have a chemical, biological or other activity of PPP1R5, including those with a similar activity or an improved activity, or with a decreased undesirable activity. Highly preferred in this regard are fragments that contain regions that are homologs in sequence, or in position, or in both sequence and to active regions of related polypeptides, such as the human $G_M$ or rat $G_L$ polypeptides. Among particularly preferred fragments in these regards are truncation mutants, as discussed above, or fragments comprising various domains of the polypeptide.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, Host Cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. Unless otherwise stated, transformation was performed as described in the method of Graham, F. and Van der Bb, A., *Virology,* 52:456–457 (1973).

The polynucleotides may be introduced alone or with other polynucleotides. Such other polynucleotides may be introduced independently, co-introduced or introduced joined to the polynucleotides of the invention. Thus, for instance, polynucleotides of the invention may be transfected into host cells with another, separate polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation may also be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al, which is illustrative of the many laboratory manuals that detail these techniques.

In accordance with this aspect of the invention the vector may be, for example, a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors may also be and preferably are introduced into cells as packaged or encapsidated virus by well known techniques for infection and transduction. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors are either supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific expression. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression, generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, bacteriophages, yeast episomes, yeast chromosomal elements, and viruses such as baculoviruses, papova viruses, SV40, vaccinia viruses, adenoviruses, fowl pox viruses, pseudorabies viruses and retroviruses, and vectors derived from combinations thereof, such as those derived from plasmid and bacteriophage genetic elements, cosmids and phagemids. Generally, any vector suitable to maintain, propagate or express polynucleotides to produce a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skilled in the art, are set forth in great detail in Sambrook et al.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous other promoters useful in this aspect of the invention are well known and may be routinely employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription. Examples include repressor binding sites and enhancers, among others. Vectors for propagation and expression generally will include selectable markers. Selectable marker genes provide a phenotypic trait for selection of transformed host cells. Preferred markers include, but are not limited to, dihydrofolate reductase or neomycin resistance for eukaryotic cell culture, and tetracycline or ampicillin resistance genes for culturing *E. coli* and other bacteria. Such markers may also be suitable for amplification. Alternatively, the vectors may contain additional markers for this purpose.

The vector containing the appropriate DNA sequence as described elsewhere herein, as well as an appropriate promoter, and other appropriate control sequences, may be introduced into an appropriate host using a variety of well known techniques suitable for expression therein of a desired polypeptide. Representative examples of appropriate hosts include bacterial cells, such as *E. coli, Streptomyces* and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts of a great variety of expression constructs are well known, and those of skill will be enabled by the present disclosure to routinely select a host for expressing a polypeptide in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of a restriction site or sites for introducing a candidate promoter fragment; i.e., a fragment that may contain a promoter. As is well known, introduction into the vector of a promoter-containing fragment at the restriction site upstream of the CAT gene engenders production of CAT activity, which can be detected by standard CAT assays. Vectors suitable to this end are well known and readily available. Two examples of such vectors include pKK232-8 and pCM7. Thus, promoters for expression of polynucleotides of the present invention include not only well known and readily available promoters, but also promoters that may be readily obtained by the foregoing technique, using a reporter gene.

Among known bacterial promoters suitable for expression of polynucleotides and polypeptides in accordance with the present invention are the *E. coli* lacI and lacZ promoters, the T3 and T7 promoters, the gpt promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous Sarcoma Virus ("RSV"), and metallothionein promoters, such as the mouse metallothionein-I promoter. Selection of appropriate vectors and promoters for expression in a host cell is a well known procedure and the requisite techniques for construction of expression vectors, introduction of the vector into the host and expression in the host are routine skills in the art.

The present invention also relates to host cells containing the above-described constructs. The host cell can be a higher eukaryotic cell, such as a mammalian cell, a lower eukaryotic cell, such as a yeast cell, or a prokaryotic cell, such as a bacterial cell. Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, the polypeptides of the invention can be synthetically produced by conventional peptide synthesizers. Mature proteins can be expressed in mammalian cells, yeast, bacteria, or other cells under the control of appropriate promoters. Cell-free translation systems can also be employed to produce such proteins using RNAs derived from the DNA constructs of the present invention.

Appropriate cloning and expression vectors for use with prokaryotic and eukaryotic hosts are described by Sambrook et al. Generally, recombinant expression vectors will include origins of replication, a promoter derived from a highly-expressed gene to direct transcription of a downstream structural sequence, and a selectable marker to permit isolation of vector containing cells following exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of *E. coli* and the trp1 gene of *S. cerevisiae*.

Transcription of DNA encoding the polypeptides of the present invention by higher eukaryotes may be increased by inserting an enhancer sequence into the vector. Enhancers are cis-acting elements of DNA, usually from about 10 to 300 bp, that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

A polynucleotide of the invention encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and a polyadenylation signal and transcription termination signal appropriately disposed at the 3' end of the transcribed region.

Appropriate secretion signals may be incorporated into the expressed polypeptide for secretion of the translated protein into the lumen of the endoplasmic reticulum, the periplasmic space or the extracellular environment. The signals may be endogenous to the polypeptide or heterologous.

The polypeptide may be expressed in a modified form, such as a fusion protein, and may include not only secretion signals but also additional heterologous functional regions. Thus, for example, a region of additional amino acids, particularly charged amino acids, may be added to the N-terminus of the polypeptide to improve stability and persistence in the host cell during purification or subsequent handling and storage. A region may also be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coli, Bacillus subtilis* and *Salmonella typhimurium*. Various species of Pseudomonas, Streptomyces, and Staphylococcus are also suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 Promega Biotec, Madison, Wis., USA). In these vectors, the pBR322 "backbone" sections are combined with an appropriate promoter and the structural sequence to be expressed.

Following transformation of a suitable host strain, the host strain is grown to an appropriate cell density. Where the selected promoter is inducible, it is induced by appropriate means (e.g., temperature shift or exposure to chemical inducer) and cells are cultured for an additional period. Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents. Such methods are well known to those skilled in the art.

Various mammalian cell culture systems can be employed for expression, as well. Examples of mammalian expression systems include, without limitation,. the C127, 3T3, CHO, HeLa, human kidney 293 and BHK cell lines. and the COS-7 line of monkey kidney fibroblasts, described by Gluzman et al., *Cell*, 23:175 (1981). Mammalian expression vectors will comprise an origin of replication, a suitable promoter and enhancer, and any necessary ribosome binding sites, polyadenylation sites, splice donor and acceptor sites, transcriptional termination sequences, and 5' flanking non-transcribed sequences that are necessary for expression. In certain preferred embodiments, DNA sequences derived from the SV40 splice sites and the SV40 polyadenylation sites are used for required non-transcribed genetic elements.

The PPP1R5 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding proteins may be employed to regenerate active conformation when the polypeptide is denatured during isolation and or purification.

Polypeptides of the present invention include naturally purified polypeptides, polypeptides produced by chemical synthetic procedures, and polypeptides produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may include an initial modified methionine residue, in some cases as a result of host-mediated processes.

PPP1R5 polynucleotides and polypeptides may be used in accordance with the present invention for a variety of applications, particularly those that make use of the chemical and biological properties of PPP1R5. Additional applications relate to diagnosis and to treatment of disorders of cells, tissues and organisms. These aspects of the invention are illustrated further by the following discussion.

Polynucleotide Assays

This invention is also related to the use of PPP1R5 polynucleotides to detect complementary polynucleotides for use, for example, as a diagnostic reagent. Detection of a mutated form of a gene encoding PPP1R5 associated with a dysfunction will provide a diagnostic tool that can add to or define diagnosis of a disease or susceptibility to a disease which results from under-expression, over-expression or altered expression of PPP1R5. Such diseases may include, for example, diseases which involve resistance to the action of insulin on glycogen synthesis. Such disorders include, without limitation, diabetes mellitus, obesity, essential hypertension, dyslipidaemia and premature atherosclerosis, among others.

Individuals carrying mutations in the human PPP1R5 gene may be detected at the DNA level by a variety of techniques. Nucleic acids for diagnosis may be obtained from a patient's cells, such as from blood, urine, saliva, tissue biopsy or autopsy material. The genomic DNA may be used directly for detection or may be amplified enzymatically by using polymerase chain reaction (PCR) [Saiki et al., Nature, 324:163–166 (1986)] prior to analysis. RNA or cDNA may also be used in similar fashion. As an example, PCR primers complementary to the nucleic acid encoding PPP1R5 can be used to identify and analyze PPP1R5 expression and mutations. For example, deletions and insertions can be detected by a change in size of the amplified product in comparison to the normal genotype. Point mutations can be identified by hybridizing amplified DNA to radiolabeled PPP1R5 RNA or, radiolabeled PPP1R5 antisense DNA sequences. Perfectly matched sequences can be distinguished from mismatched duplexes by RNase A digestion or by differences in melting temperatures.

Sequence differences between a reference gene and genes having mutations may also be revealed by direct DNA sequencing. In addition, cloned DNA segments may be employed as probes to detect specific DNA segments. The sensitivity of such methods can be greatly enhanced by appropriate use of PCR or other amplification methods. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alterations in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures [see, e.g., Myers et al., Science, 230:1242 (1985)].

Sequence changes at specific locations may also be revealed by nuclease protection assays, such as RNase and S1 protection or the chemical cleavage method [e.g., Cotton et al., Proc. Natl. Acad. Sci. USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

The invention provides a process for diagnosing or determining a susceptibility to PPP1R5-related dysfunctions or diseases including, but not limited to, diseases which involve resistance to the action of insulin on glycogen synthesis. Such disorders include, without limitation, diabetes mellitus, obesity, essential hypertension, dyslipidaemia and premature atherosclerosis, among others. A mutation in the PPP1R5 gene indicates a susceptibility to such dysfunctions or diseases and the nucleic acid sequences described above may be employed in an assay for ascertaining such susceptibility. Thus, for example, the assay may be employed to determine a mutation in a human PPP1R5 gene as herein described, such as a substitution, deletion, truncation, insertion, frame shift, etc., with such mutation being indicative of a susceptibility to any of the dysfunctions or diseases recited above.

The invention provides a process for diagnosing such aforementioned PPP1R5-related diseases comprising determining from a sample derived from a patient an abnormally decreased or increased level of expression of polynucleotide having the sequence of FIGS. 1A–1B [SEQ ID NO: 1]. Decreased or increased expression of polynucleotide can be measured using any of the methods well known in the art for the quantitation of polynucleotides, such as, for example, PCR, RT-PCR, RNase protection, Northern blotting and other hybridization methods. In addition to more conventional gel-electrophoresis and DNA sequencing, mutations can also be detected by in situ analysis.

Chromosome Assays

The sequences of the present invention are also valuable for chromosome identification. The sequence is specifically targeted, to and can hybridize with, a particular location on an individual human chromosome. Moreover, there is a current need for identifying particular sites on the chromosome. Few chromosome marking reagents based on actual sequence data (repeat polymorphisms) are presently available for marking chromosomal location.. The mapping of DNAs to chromosomes according to the present invention is an important first step in correlating those sequences with gene associated disease.

Briefly, sequences can be mapped to chromosomes by preparing PCR primers (preferably 15–30 bp) from the cDNA. Computer analysis of the 3' untranslated region is used to rapidly select primers that do not span more than one exon in the genomic DNA, because primers that span more than one exon could complicate the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can be used similarly to map to the chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNAs as short as 50 to 60 bases. For a review of this technique, see Verma et al., HUMAN CHROMOSOMES: A MANUAL OF BASIC TECHNIQUES, PERGAMON PRESS, NEW YORK, 1988.

As an example of how this technique is performed, human PPP1R5 DNA is digested and purified with QIAEX II DNA purification kit (QIAGEN, Inc., Chatsworth, Calif.) and ligated to Super Cos1 cosmid vector (STRATAGENE, La Jolla, Calif.). DNA is purified using Qiagen Plasmid Purification Kit (QIAGEN Inc., Chatsworth, Calif.) and 1 mg is labeled by nick translation in the presence of Biotin-dATP using BioNick Labeling Kit (GibcoBRL, Life Technologies Inc., Gaithersburg, Md.). Biotinylation is detected with GENE-TECT Detection System (CLONTECH Laboratories, Inc. Palo Alto, Calif.). In situ hybridization is performed on slides using ONCOR Light Hybridization Kit (ONCOR, Gaithersberg, Md.) to detect single copy sequences on metaphase chromosomes. Peripheral blood of normal donors is cultured for three days in RPMI 1640 supplemented with 20% FCS, 3% PHA and penicillin/streptomycin, synchronized with 10–7 M methotrexate for 17 hours, and washed twice with unsupplemented RPMI. Cells are then incubated with 10–3 M thymidine for 7 hours. The cells are arrested in metaphase after a 20 minute incubation with colcemid (0.5 mg/ml) followed by hypotonic lysis in 75 mM KCl for 15 minutes at 37° C. Cell pellets are then spun out and fixed in Carnoy's fixative (3:1 methanol/acetic acid).

Metaphase spreads are prepared by adding a drop of the suspension onto slides and air drying the suspension. Hybridization is performed by adding 100 ng of probe suspended in 10 ml of hybridization mix (50% formamide, 2xSSC, 1% dextran sulfate) with blocking human placental DNA (1 mg/ml). Probe mixture is denatured for 10 minutes in a 70° C. water bath and incubated for 1 hour at 37° C., before placement on a prewarmed (37° C.) slide, previously denatured in 70% formamide/2xSSC at 70° C., dehydrated in ethanol series, and chilled to 4° C.

Slides are incubated for 16 hours at 37° C. in a humidified chamber. Slides are washed in 50% formamide/2xSSC for 10 minutes at 41° C. and 2xSSC for 7 minutes at 37° C. Hybridization probe is detected by incubation of the slides with FITC-Avidin (ONCOR, Gaithersberg, Md.), according to the manufacturer's. protocol. Chromosomes are counterstained with propridium iodine suspended in mounting medium. Slides are visualized using a Leitz ORTHOPLAN 2-epifluorescence microscope and five computer images are taken using a Imagenetics Computer and MacIntosh printer.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

It is then necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes assuming 1 megabase mapping resolution and one gene per 20 kb.

Another method of chromosomal location, which was described in Example 1, involves overlap of current cDNA with an assembly of cDNA derived from an EST database. This method allowed the discovery that the entire cDNA matched known PCR primer pairs. The extreme 3' sequence overlapped two sequence tagged site sequences (STS identifiers: WI-11129 and TIGR-A004S47) which have been localized to chromosome 10q23-24.

Polypeptide Assays

The present invention also relates to diagnostic assays for detecting levels of PPP1R5 protein in cells and tissues. Such assays may be quantitative or qualitative, Thus, for instance, a diagnostic assay in accordance with the invention for detecting over-expression of PPP1R5 protein compared to normal control tissue samples may be used to detect the presence of a disease/disorder such as those above-recited. Assay techniques that can be used to determine levels of a protein, such as an PPP1R5 protein of the present invention, in a sample derived from a host are well-known to those of skill in the art. Such assay methods include radioimmunoassays, competitive-binding assays, Western Blot analysis and ELISA assays. Among these, ELISAs are frequently preferred. An ELISA assay initially comprises preparing an antibody specific to PPP1R5, preferably a monoclonal antibody. In addition a reporter antibody generally is prepared which binds to the monoclonal antibody. The reporter antibody is attached to a detectable reagent such as a radioactive, fluorescent or enzymatic reagent, in this example, horseradish peroxidase enzyme.

To carry out an ELISA, a sample is removed from a host and incubated on a solid support, e.g. a polystyrene dish, that binds the proteins in the sample. Any free protein binding sites on the dish are then covered by incubating with a non-specific protein such as bovine seruim albumin. The monoclonal antibody is then incubated in the dish during which time the monoclonal antibodies attach to any PPP1R5 proteins attached to the polystyrene dish. Unbound monoclonal antibody is washed out with buffer. The reporter antibody linked to horseradish peroxidase is placed in the dish resulting in binding of the reporter antibody to any monoclonal antibody bound to PPP1R5. Unattached reporter antibody is then washed out. Reagents for peroxidase activity, including a colorimetric substrate, are then added to the dish. Immobilized peroxidase, linked to PPP1R5 through the primary and secondary antibodies, produces a colored reaction product. The amount of color developed in a given time period indicates the amount of PPP1R5 protein present in the sample. Quantitative results typically are obtained by reference to a standard curve.

A competition assay may also be employed wherein antibodies specific to PPP1R5 are attached to a solid support and labeled PPP1R5 and a sample derived from the host are passed over the solid support. The amount of detected label attached to the solid support can be correlated to a quantity of PPP1R5 in the sample.

Various options are available for formatting an enzyme assay. Such assays enable one to insert into the system an unknown compound, which can inhibit the reaction by interacting with the PPP1R5 polypeptide or with PP1. The choice of format depends upon the sensitivity required and the purpose of the assay: whether it is designed to quantitate enzyme levels or to measure inhibition in kinetic studies. Regardless of format, such enzyme assays are advantageous both for automation and for high throughput screening.

Antibodies

The polypeptides, their fragments or other derivatives, or analogs thereof, or cells expressing them can also be used as immunogens to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique [G. Kohler and C. Milstein, *Nature,* 256:495–497 (1975)], the trioma technique, the human B-cell hybridoma technique Kozbor et al., *Immunology Today* 4:72 (1983)], and the EBV-hybridoma technique [Cole et al., MONOCLONAL ANTIBODIES AND CANCER THERAPY, pg. 77–96, Alan R. Liss, Inc., (1985)].

Techniques described for the production of single chain antibodies [U.S. Pat. No. 4,946,778] can also be adapted to produce single chain antibodies to immunogenic polypeptide products of this invention. Also, transgenic mice, or other organisms including other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Antibodies against PPP1R5 may also be employed to inhibit dysfunctions or diseases which involve resistance to the action of insulin on glycogen synthesis such as those disorders identified above.

PPP1R5 Binding Molecules and Assays

PPP1R5 can be used to isolate proteins which interact with it; and this interaction can be a target for interference. Inhibitors of protein-protein interactions between PPP1R5 and PP1 or other factors could lead to the development of pharmaceutical agents for the modulation of PPP1R5 activity.

Thus, this invention also provides a method for identification of binding molecules to PPP1R5, in addition to PP1. Genes encoding proteins for binding molecules to PPP1R5 can be identified by numerous methods known to those of skill in the art, for example, ligand panning and FACS sorting. Such methods are described in many laboratory manuals such as, for instance, Coligan et al., CURRENT PROTOCOLS IN IMMUNOLOGY 1, Chapter 5 (1991).

For example, the yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, PPP1R5 cDNA is fused to a Ga14 transcription factor DNA binding domain and expressed in yeast cells. cDNA library members obtained from cells of interest are fused to a transactivation domain of Ga14. cDNA clones which express proteins which can interact with PPP1R5 will lead to reconstitution of Ga14 activity and transactivation of expression of a reporter gene such as Ga11-lacZ.

An alternative method involves screening of lambda gt11 or lambda ZAP (Stratagene) or equivalent cDNA expression libraries with recombinant PPP1R5. Recombinant PPP1R5 protein or fragments thereof are fused to small peptide tags such as FLAG, HSV or GST. The peptide tags can possess convenient phosphorylation sites for a kinase such as heart muscle creatine kinase or they can be biotinylated. Recombinant PPP1R5 can be phosphorylated with $^{32}[P]$ or used unlabeled and detected with streptavidin or antibodies against the tags. Lambda gt11 cDNA expression libraries are made from cells of interest and are incubated with the recombinant PPP1R5, washed and cDNA clones which interact with PPP1R5 isolated. Such methods are routinely used by skilled artisans. See, e.g., Sambrook et al, cited above.

Another method is the screening of a mammalian expression library. In this method, cDNAs are cloned into a vector between a mammalian promoter and polyadenylation site and transiently transfected in COS or 293 cells. Forty-eight hours later, the binding protein is detected by incubation of fixed and washed cells with labeled PPP1R5. In a preferred embodiment, the PPP1R5 is iodinated, and any bound PPP1R5 is detected by autoradiography. See Sims et al., *Science,* 241:585–589 (1988) and McMahan et al., *EMBO J,* 10:2821–2832 (1991). In this manner, pools of cDNAs containing the cDNA encoding the binding protein of interest can be selected and the cDNA of interest can be isolated by further subdivision of each pool followed by cycles of transient transfection, binding and autoradiography.

If the binding protein is secreted, its cDNA can be obtained by a similar pooling strategy once a binding or neutralizing assay has been established for assaying supernatants from transiently transfected cells. General methods for screening supernatants are disclosed in Wong et al., *Science,* 228:810–815 (1985).

Another method involves isolation of proteins interacting with PPP1R5 directly from cells. Fusion proteins of PPP1R5 with GST or small peptide tags are made and immobilized on beads. Biosynthetically labeled or unlabeled protein extracts from the cells of interest are prepared, incubated with the beads and washed with buffer. Proteins interacting with PPP1R5 are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another method is immunoaffinity purification. Recombinant PPP1R5 is incubated with labeled or unlabeled cell extracts and immunoprecipitated with anti-PPP1R5 antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method involves screening of peptide libraries for binding partners. Recombinant tagged or labeled PPP1R5 is used to select peptides from a peptide or phosphopeptide library which interact with PPP1R5. Sequencing of the peptides leads to identification of consensus peptide sequences which might be found in interacting proteins.

Agonists and Antagonists—Assays and Molecules

The PPP1R5 of the present invention may be employed in a screening process for compounds which activate (agonists) or inhibit activation (antagonists) of the PPP1R5 polypeptides of the present invention.

One method for screening for agonists or antagonists involves mixing an epitope tagged version of PPP1R5, such as the GST-PPP1R5 described in FIG. 3, and purified PP1 and measuring their binding to each other in the presence or absence of the putative antagonist. This binding assay may be in the form of an ELISA plate assay, set up in the following manner.

The GST-PPP1R5 is adhered to the plate directly or via an anti-GST antibody, followed by blocking of additional binding sites with a non-specific protein such as Bovine Serum Albumin. The wells are then incubated with PP1 in the presence or absence of the antagonist. After a wash step, the bound PP1 can be detected via a specific antibody indirectly or directly linked to an enzyme such as horseradish peroxidase or alkaline phosphatase. An antagonist will reduce the amount of binding, whereas an agonist will increase it. Manipulation of the level of each protein to enhance the detection of such agonists and antagonists is known to practitioners in the art.

The assay could also be configured with PP1 on the plate and GST-PPP1R5 or PPP1R5 added in the presence of antagonist or agonist. In addition to antibody detection of PPP1R5 or GST-PPP1R5 bound to the plate, one could also measure the activity of PP1 on the plate, since it would be inhibited by bound PPP1R5.

There are other binding formats known to those of skill in the art, including coprecipitation (e.g., Example 3 below) and surface plasmon resonance. Similar assays could be configured to measure the interaction of PPP1R5 with other proteins, glycogen, and non-protein entities that might be discovered using the previously described methods.

Methods for detecting agonists or antagonists for the PPP1R5 of the present invention include the yeast based technology as described in U.S. Pat. No. 5,482,835.

Examples of potential PPP1R5 antagonists include antibodies or, in some cases, peptides which bind to the PPP1R5 but do not elicit a response such that the activity of the PPP1R5 is prevented.

Potential antagonists also include proteins which are closely related to a ligand of PPP1R5, i.e., a fragment of the ligand, which proteins have lost biological function and, when binding to PPP1R5, elicit no response.

A potential antagonist also includes an antisense construct prepared through the use of antisense technology. Antisense technology can be used to control gene expression through triple-helix formation or antisense DNA or RNA, both methods of which are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix) [see, Lee et al., Nucl. Acids Res., 6:3073 (1979); Cooney et al., Science, 241:456 (1988); and Dervan et al., Science, 251:1360 (1991)], thereby preventing transcription and production of the PPP1R5. The antisense RNA oligonucleotide hybridizes to the mRNA in vivo and blocks translation of the mRNA molecule into the PPP1R5 (antisense) [Okano, J. Neurochem., 56:560 (1991); and OLIGODEOXYNUCLEOTIDES AS ANTISENSE INHIBITORS OF GENE EXPRESSION, CRC Press, Boca Raton, Fla. (1988)]. The oligonucleotides described above can also be delivered to cells such that the antisense RNA or DNA is expressed in vivo to inhibit production of the PPP1R5.

Another potential antagonist is a small molecule which binds to PPP1R5, making it inaccessible to PP1 such that normal biological activity is prevented. Examples of small molecules include, but are not limited to, small peptides or peptide-like molecules: The small molecules may also bind the PPI or another interaction protein of the PPP1R5 polypeptide to prevent binding. Examples of small molecules include but are not limited to small peptides or peptide-like molecules.

Potential antagonists also include fragments of the PPP1R5, which bind to the ligand and prevent the ligand from interacting with the cytoplasmic PPP1R5. PPP1R5 proteins are ubiquitous in the mammalian host and are responsible for mediating many biological functions, including many pathologies. Accordingly, it is desirous to find compounds and drugs which stimulate PPP1R5 on the one hand, and which can inhibit the function of PPP1R5 on the other hand. In general, agonists or antagonists for PPP1R5 are employed for therapeutic and prophylactic purposes for such diseases or disorders as those detailed hereinbefore, among others.

This invention additionally provides a method of treating an abnormal condition related to an excess of PPP1R5 activity which comprises administering to a subject an inhibitor compound (antagonist) as hereinabove described along with a pharmaceutically acceptable carrier in an amount effective to inhibit activation by blocking binding of ligands to the PPP1R5, or by inhibiting a second signal, and thereby alleviating the abnormal condition.

The invention also provides a method of treating abnormal conditions related to an under-expression of PPP1R5 and its activity, which comprises administering to a subject a therapeutically effective amount of a compound which activates the PPP1R5 polypeptide of the present invention (agonist) as described above, in combination with a pharmaceutically acceptable carrier, to thereby alleviate the abnormal condition.

Compositions and Kits

These PPP1R5 polypeptides, and compounds which activate or inhibit such PPP1R5, may be employed in combination with a suitable pharmaceutical, physiologically acceptable carrier. Such compositions comprise a therapeutically effective amount of the polypeptide or compound, and a pharmaceutically acceptable carrier or excipient. Such carriers include but are not limited to, saline, phosphate, buffered saline, dextrose, sterilized water, glycerol, ethanol, and combinations thereof. The formulation should suit the mode of administration. Selection of an appropriate carrier in accordance with the mode of administration is routinely performed by those skilled in the art.

The invention further relates to pharmaceutical packs and kits comprising one or more containers filled with one or more of the ingredients of the aforementioned compositions of the invention.

Administration

Certain disease pathologies may be partially or completely ameliorated by the systemic clinical administration of the PPP1R5 polypeptides of this invention. This administration can be in the form of gene therapy (see below) or through the administration of PPP1R5 peptides agonists or antagonists synthesized from recombinant constructs of PPP1R5 DNA or from peptide chemical synthesis [Woo et al., Protein Engineering, 3:29–37 (1989)].

Polypeptides and other compounds of the present invention which activate or inhibit PPP1R5 may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes, among others.

The pharmaceutical compositions generally are administered in an amount effective for treatment or prophylaxis of a specific indication or indications. The amount employed of the subject polypeptide or compound will vary with the manner of administration, the employment of other active compounds, and the like, generally being in the range of about 1 mg to 100 mg. The amount of compound employed will be determined empirically, based on the response of cells in vitro and response of experimental animals to the subject polypeptides or formulations containing the subject polypeptides. In general, the compositions are administered in an amount of at least about 10 mg/kg body weight. In most cases they will be administered in an amount not in excess of about 8 mg/g body weight per day. Preferably, in most cases, the administered dose is from about 10 mg/kg to about 1 mg/kg body weight, daily. It will be appreciated that optimum dosage will be determined by standard methods for each treatment modality and indication, taking into account the indication, its severity, route of administration, complicating conditions and the like.

Gene Therapy

The PPP1R5 polynucleotides, polypeptides, agonists and antagonists that are polypeptides may be employed in accordance with the present invention by expression of such polypeptides in treatment modalities often referred to as "gene therapy". Thus, for example, cells from a patient may be engineered with a polynucleotide, such as a DNA or RNA, to encode a polypeptide ex vivo. The engineered cells can then be provided to a patient to be treated with the polypeptide. In this embodiment, cells may be engineered ex vivo, for example, by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector or adenoviral vector or other vector (e.g., poxvirus vectors). The expression construct may then be isolated. A packaging cell is transduced with a plasmid vector containing RNA encoding a polypeptide of the present invention, such that the packaging cell now produces infectious viral particles containing the gene of interest. These producer cells may be administered to a patient for engineering cells in vivo and expression of the polypeptide in vivo. These and other methods for administering a polypeptide of the present invention should be apparent to those skilled in the art from the teachings of the present invention.

Retroviruses from which the retroviral plasmid vectors hereinabove-mentioned may be derived include, but are not limited to, Moloney Murine Leukemia Virus, Spleen Necrosis Virus, Rous Sarcoma Virus, Harvey Sarcoma Virus, Avian Leukosis Virus, Gibbon Ape Leukemia Virus, Human Immunodeficiency Virus, Adenovirus, Myeloproliferative Sarcoma Virus, and Mammary Tumor Virus. In a preferred embodiment, the retroviral plasmid vector is derived from Moloney Murine Leukemia Virus.

Such vectors will include one or more promoters for expressing the polypeptide. Suitable promoters which may be employed include, but are not limited to, the retroviral LTR; the SV40 promoter; and the human cytomegalovirus (CMV) promoter described in Miller et al., Biotechniques, 7:980–990 (1989). Cellular promoters such as eukaryotic cellular promoters including, but not limited to, the histone, RNA polymerase III, and b-actin promoters, can also be used. Additional viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the b-actin promoter; and human growth hormone promoters. The promoter may also be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E-86, GP+envAm12, and DAN cell lines as described in Miller, A., Human Gene Therapy, 1990, 1:5–14. The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles may then be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples, which are provided solely to illustrate the invention by reference to specific embodiments. These exemplifications do not limit or circumscribe the scope of the disclosed invention. Certain terms used herein are explained in the foregoing glossary. All examples are carried out using standard techniques, which are well known and routine to those of skill in the art, except where otherwise described in detail. Routine molecular biology techniques of the following examples can be carried out as described in standard laboratory manuals, such as Sambrook et al. All parts or amounts set out in the following examples are by weight, unless otherwise specified.

Example 1
Identification and Sequence Analysis of the cDNA Encoding Human Protein Phosphatase 1 Binding Subunit R5

A human genome expressed sequence (EST) database, derived from over 500 human cDNA libraries [M. Adams et al, *Nature,* 355:632–634 (1992); M. Adams et al, *Nature,* 377:3–174 (1995)] was searched for sequences related to the rat liver glycogen binding subunit ($G_L$) using the TBLASTN algorithm [S. F. Altschul et al, *J. Mol. Biol.,* 215:403–410 (1990)]. Four overlapping, partially sequenced, cDNA sequences, identified from different libraries encoded part of a protein with significant sequence similarities to rat $G_L$. The protein was called PPP1R5. One of these cDNAs pHGBDX21, which encoded PPP1R5 and was derived from a human gall bladder library, was completely sequenced in both directions on an Applied Biosystems 373A automated DNA sequencer using Taq dye terminator cycle sequencing. The complete sequence of the open reading frame encoded by the pHGBDX21 cDNA is presented in FIGS. 1A–1B [SEQ ID NO: 1].

The complete sequence of FIGS. 1A–1B was searched against a more recent update of the EST library organize into overlapping assemblies, and this identified 58 further ESTs which spanned the entire coding region and an additional 379 nucleotides (or 1.38 kb) of 3' untranslated region (UTR) not included in the original cDNA. Hence the entire mRNA is at least 2.5 kb. The extreme 3' UTR sequence also overlapped two tagged site sequences (STS identifiers: WI-11129 and TIGR-A004S47) which allows the gene for PPP1R5 to be localized to chromosome 10q23-24 [Whitehead/MIT Center].

The predicted PPP1R5 protein of FIGS. 1A–1B is 36.4 kDa, comprising 317 amino acids, if the initiating methionine is at codon 1 rather than codon 6, 20 or 26. An inframe termination codon precedes codon 1. However, nucleotide sequences immediately preceding codons 6, 20 and 26 conform more closely to the consensus sequence for eukaryote translation initiation [M. Kozak, *J. Biol. Chem.,* 266:19867–19870 (1991)] than that preceding codon 1. Translation may therefore start at codon 6 of SEQ ID NO: 2 (FIG. 1B), giving rise to a 312 amino acid protein of 35.8 kDa. It is also possible that translation starts at amino acid 20, giving rise to a protein of 298 amino acids, or at amino acid 26, giving rise to a protein of 292 amino acids.

The amino acid sequence of human PPP1R5 shows 42% identity to rat liver $G_L$ and 51% similarity if conservative substitutions are taken into account (FIG. 2). PPP1R5 is less similar to $G_M$ showing only 27% and 28% identity to the first 285 amino acids of rabbit and human $G_M$, respectively. The low degree of similarity of PPP1R5 to $G_L$ and $G_M$ indicates that PPP1R5 is unlikely to be the human homolog of rat $G_L$. The glycogen binding subunits from human and rabbit skeletal muscle show a much higher level of identity (73%) [Chen et al., (1994), cited above].

The different tissue distributions of human PPP1R5 and rat $G_L$ also indicate that these two proteins are not species homologs. PPP1R5 cDNA was identified in cDNA libraries from several adult tissues and cells, including gall bladder, prostate, osteoblasts, retina, smooth muscle, liver, kidney, medulla, striatum and senescent fibroblasts, several fetal tissues including brain, lung, liver, heart, spleen and placenta, and tumor cells such as osteosarcoma, hepatocellular, ovarian and melanocyte tumor cells. Additionally, a liver cDNA kindly provided by I.M.A.G.E. consortium, St. Louis was shown by sequence analysis to encode part of PPP1R5.

In contrast, $G_L$ appeared to be a liver specific protein since its mRNA was present in liver but undetectable in lung, brain, heart, spleen, skeletal muscle, kidney and testis [Doherty et al. (1995) cited above].

Thus, human protein phosphatase 1 binding subunit R5 is related to, but not the homolog of, rat liver glycogen binding subunit of PP1.

Example 2
Expression of GST-PPP1R5 Fusion Protein in *E. coli* and Production of Antibodies In order to determine whether PPP1R5 would bind to PP1, R5 was expressed in *E. coli* as a GST fusion protein as follows. The open reading of PPP1R5 was amplified by PCR using oligonucleotide 5'-CGCCATATGAGCTGCACCAGAATGATC-3' [SEQ ID NO: 7], which creates an Nde I site (underlined) at the initiating methionine codon and oligonucleotide 5'-CGCCTCGAGTCATCGATAAGAGGCCAAGTTC-3' [SEQ ID NO: 8], which creates an XhoI site (underlined) just 3' of the termination codon. The complete coding region of PPP1R5 was cloned into the prokaryote gene fusion expression vector pGEX-CA [Guan and Dixon, *Anal. Biochem.* 192:262–267 (1991); Doherty et al, (1995) cited above]. The final construct, pGEX-PPP1R5, encoded glutathione-S- transferase (GST) followed by the complete open reading frame of PPP1R5.

The pGEX-PPP1R5 plasmid was transfected into *E. coli* by conventional techniques, the transfectants cultured under appropriate culture conditions, and GST-PPP1R5 (or GST-R5) fusion protein expressed in *E. coli*. The GST-PPP1R5 protein was purified from the culture by affinity chromatography on glutathione-agarose (Sigma) as described in Doherty et al., (1995) cited above. 250 mg of soluble GST-PPP1R5 was isolated per liter of bacterial culture.

Antibodies to GST-PPP1R5 were raised in sheep and affinity purified. For measurement of the effect of PPP1R5 on the PP1 activity, contaminating GST in the GST-PPP1R5 preparation was removed by chromatography on Superdex 200 in 50 mM Tris-HCl, pH7.5, 0.03% Brij-35, 0.1% 2-mercaptoethanol. GST-PPP1R5 eluted as a dimer, probably because GST possesses a dimeric structure.

Additionally, affinity purified antibodies to GST-PPP1R5 recognized a 36kDa protein on the immunoblot or rat liver and skeletal muscle extracts, whereas $G_L$ (33kDa) was only detected in liver.

Example 3
Human PPP1R5 Coprecipitates with PP1.

Glutathione-affinity precipitation studies were performed as follows. The purified GST-PPP1R5 was obtained as described in Example 2. Human PP1g [Barker et al, *Biochim. Biophys. Acta* 1178:228–233 (1993)] was expressed in *E. coli* and purified as described in Alessi et al., (1993), cited above. Differing amounts of GST-PPP1R5 and bacterially expressed PP1 were incubated in 50 or 100 ml of 50 mM Tris-HCl, pH7.5, containing 150 mM NaCl, 0.1% (v/v) 2-mercaptoethanol, 0.02% (v/v) Brij 35 and 0.1 mg/ml bovine serum albumin for 1 hour at 4° C. 10 ml of glutathione-agarose beads (Sigma) was added and incubation was continued at 4° C. with shaking for 30 minutes. After centrifigation, the supernatant was removed and the pellet washed twice with 1 ml buffer (without albumin), then denatured by heating in SDS gel loading buffer at 95° C. for 5 minutes and analyzed by polyacrylamide gel electrophoresis.

SDS polyacrylamide gel analysis of the pellets showed that PP1 was precipitated in the presence of GST-PPP1R5 and GSH-agarose beads but not in control incubations containing only PP1 and GSH agarose (data not shown).

Example 4
Human PPP1R5 Modulates the Substrate Specificity of PP1.

Protein phosphatase assays were performed in the absence of divalent cations as described in Cohen et al, (1988), cited above. The catalytic subunit PP1g, described above in Example 2, was diluted in assay buffer to 1.5 U/ml (1.4 nM). Rabbit skeletal muscle glycogen phosphorylase was $^{32}$P-labelled by phosphorylase kinase to a stoichiometry of 1 mol phosphate per mol subunit as in Cohen et al, *Meth. Enzymol.* 159:390–408 (1988) and was 10 mM in the assays.

A 0.01 ml aliquot was incubated for 15 minutes at 30° C. with 0.01 ml of the concentrations (0.01, 0.1, 1, 10, 100, 1000 nM) of the purified bacterially expressed GST-R5, GST-$G_L$ or GST diluted in the same buffer. Assays were initiated with 0.01 ml $^{32}$P-labelled phosphorylase. One unit of activity is the amount of enzyme which catalyses the release of 1 mmol of [$^{32}$P]phosphate per minute.

As shown in FIG. 3, affinity purified GST-PPP1R5 inhibited the phosphorylase phosphatase activity of PP1 as observed previously for GST-$G_L$ [Doherty et al, (1995) cited above]. The amount of inhibition varied with the different preparations of GST-R5 and GST $G_L$, probably due to the aggregation of both protein preparations. FIG. 3 shows that inhibition observed with freshly prepared preparation of GST-R5 and GST-$G_L$ was similar with an IC$_{50}$ of approximately 100 nM. Removal of GST, which was a major contaminant of the PPP1R5 preparation, did not significantly affect the IC$_{50}$.

Example 5
Human PPP1R5 does not Bind Phosphorylase a.

The glycogen synthase phosphatase activity of the complex of PP1 with $G_L$ is inhibited by phosphorylase a, the inhibition being achieved by the binding of phosphorylase a to the $G_L$ submit [Doherty et al. (1995) cited above]. PPP1R5 was therefore tested for its ability to bind phosphorylase a.

An immunoblot was prepared, comparing the binding of phosphorylase a to GST-$G_L$ and GST-R5. GST-R5 and GST-$G_L$ were electrophoresed on a 10% polyacrylamide gel, transferred to nitrocellulose membranes and either (A) probed with 0.01 ml $^{32}$P labelled phosphorylase a as described in Doherty et al, (1995), cited above and Moorhead et al., (1995), cited above or (B) stained with Coomassie blue. One lane ran the affinity-purified GST-$G_L$; a second lane ran affinity purified GST- R5; a third lane ran GST-R5 after gel filtration on Superdex 200 for each condition (A) and (B). The molecular mass markers were phosphorylase β (97 kDa), bovine serum albumin (66 kDa), ovalbumin (43 kDa) and carbonic anhydrase (29 KDa).

The results of the immunoblot (not shown) indicate that phosphorylase a bound to GST-$G_L$ [i.e., a large blot appeared in lane 1(A) between the 43 and 66 kDa markers]. However, phosphorylase a did not bind to GST-PPP1R5 [i.e., no blots appears in lanes 2 and 3 of condition (A)]. Under condition (B), a small blot appeared in lane 1 between the 43 and 66 kDa markers, and medium sized blots appeared in lane 2 [i.e., two blots appeared between the 43 and 66 kDa markers; and one blot appeared between the 20 and 29 kDa markers. One blot appeared between the 43 and 66 kDa markers in Lane 3(B)].

Thus, PPP1R5 is distinct from $G_L$ in this property and is not regulated by phosphorylase a.

Example 6
Expression of PPP1R5 in Mammalian Cells

An expression plasmid is made by cloning a cDNA encoding PPP1R5 into the expression vector pCDN [N. Aiyar et al, *Mol. Cell. Biochem.,* 131:75–86 (1994), incorporated by reference herein]. The selection of suitable restriction enzymes and techniques for cloning are well-known to those of skill in the art.

The expression vector pCDN contains:

(1) a human cytomegalovirus (CMV) promoter, a bovine growth hormone 3' flanking sequence, a polylinker, an SV40 intron, and a polyadenylation signal arranged so that a cDNA can be conveniently placed under expression control of the CMV promoter and operably linked to the SV40 intron and the polyadenylation signal by means of restriction sites in the polylinker;

(2) an *E. coli* origin of replication effective for propagation in *E. coli* and other prokaryotic cells;

(3) a bacterial neomycin phosphotransferase gene (NEO) expression cassette for geneticin (G418) selection;

(4) a murine dihydrofolate reductase (DHFR) expression cassette for methotrexate (MTX) amplification;

(5) ampicillin resistance gene for selection of plasmid-containing prokaryotic cells; and (6) an SV40 origin of replication for propagation in eukaryotic cells.

A DNA fragment encoding the entire PPP1R5 is cloned into the polylinker region of the vector so that recombinant protein expression is directed by the CMV promoter. The plasmid construction strategy is as follows.

The PPP1R5 cDNA of the plasmid is amplified using primers that contain unique restriction sites. To maximize receptor expression, 5' and 3' untranslated regions (UTRs) are removed from the receptor cDNA using the unique restriction enzyme prior to insertion into the vector pCDN. Since PCR is used to trim the cDNAs, the DNA sequences are confirmed prior to expression.

Suitable primers are used in this example. The 5' primer is about 30 bp in length and contains the unique restriction site and an AUG start codon. The 3' primer, contains about 30 bp and a suitable STOP codon.

The PCR amplified DNA fragment and the vector, pCDN, are digested with the restriction enzymes unique to this sequence and then ligated. The ligation mixture is transformed into *E coli* strain SURE (available from Stratagene Cloning Systems, La Jolla, Calif. 92037) the transformed culture is plated on ampicillin media plates which are then incubated to allow growth of ampicillin resistant colonies.

Plasmid DNA is isolated from resistant colonies and examined by restriction analysis and gel sizing for the presence of the PPP1R5-encoding fragment.

Human embryonic kidney 293 (HEK293) cells are selected to express the HTABK54 receptor. For expression of recombinant HTABK54, $2 \times 10^5$ HEK 293 cells are plated in media and incubated overnight at 37° C. in a 5% humidified incubator. The next day, 20 mg/plate of the expression vector, as described above, DNA is introduced into the cells by the calcium phosphate procedure using a mammalian transfection kit according to the manufacturer's instructions, or using DEAE-DEXTRAN, as described, for instance, in Sambrook et al, cited above.

Following transfection, the cells were incubated at 37° C. in 3% $CO_2$ for 24 hours, washed with warm Dulbecco's phosphate buffered saline (DPBS) fed with fresh media and maintained at 37° C. in 5% $CO_2$. After overnight incubation, the media is removed and replaced with fresh selection media that contains 400 mg/ml G418 to select for cells that are stably transformed with the expression vector. Selection media is replaced twice weekly for 2–4 weeks until independent cell colonies appear on the dishes. Cell colonies are individually picked and purified by limited dilution, and expanded for further analysis. The clones are grown in 6 well plates and a clonal cell line expressing human PPP1R5 is identified.

Expression is detected by Northern blot analysis. An expression product of the expected size is seen in the cell lysate, which is not seen in negative controls (HEK293 cell clones transfected with pCDN vector alone serve as negative controls).

Example 7
Identification of Ligands or Antagonists

The expressed PPP1Rt described above in Examples 1 or 6 is then screened for ligands or antagonists as follows.

A. Ligand/Tissue Banks

The expressed PPP1R5 is utilized to screen compound banks, complex biological fluids, combinatorial organic and peptide libraries, etc. to identify activating ligands or antagonists. For example, the expressed PPP1R5 is employed to screen a bank of over 150 putative orphan ligands, which comprises (a) naturally occurring compounds which may be putative agonists or antagonists for PPP1R5; (b) non-mammalian, biologically active peptides for which there may be as yet undiscovered mammalian counterparts, such as savagine, urotensin 1, (c) compounds not found in nature, but which appear to activate PP1 binding subunits with unknown natural ligands (e.g., delta 9THC) and others.

Similarly, the PPP1R5 is screened against tissue extracts of human, and other mammalian, species, such as porcine tissue. Specifically such tissue extracts include lung, liver, gut, heart, kidney, adrenals, ischemic brain, plasma, urine and placenta. Initial extraction procedures focus on removal of bulk protein via acid or ethanol precipitation to bias the separation towards peptides and small molecules that account for a high percentage of known natural ligands of PPP1R5. Subsequently milder extraction procedures are used to identify proteins. Extraction techniques employed in the formation of these tissue banks are known in the art.

B. ELISA Plate Assay

The GST-PPP1R5 is adhered to the ELISA plate directly or via an anti-GST antibody, followed by blocking of additional binding sites with a non-specific protein, e.g., BSA. The wells are incubated with PP1 in the presence or absence of the antagonist. After a wash step, the bound PP1 is detected via a specific antibody indirectly or directly linked to an enzyme, such as horseradish peroxidase or alkaline phosphatase. An antagonist reduces the amount of binding, whereas an agonist increases it. Manipulation of the level of each protein to enhance the detection of such agonists and antagonists is known to the art.

The assay can be configured with PP1 on the plate and GST-PPP1R5 or PPP1R5 added in the presence of antagonist or agonist. In addition to antibody detection of PPP1R5 or GST-PPP1R5 bound to the plate, the activity of PP1 on the plate is measured, since it is inhibited by bound PPP1R5.

Example 8
Expression of Human PPP1R5 for Gene Therapy

Fibroblasts are obtained from a subject by skin biopsy. The resulting tissue is placed in tissue-culture medium and separated into small pieces. Small chunks of the tissue are placed on a wet surface of a tissue culture flask; approximately ten pieces are placed in each flask. The flask is turned upside down, closed tight and left at room temperature overnight. After 24 hours at room temperature, the flask is inverted; the chunks of tissue remain fixed to the bottom of the flask; and fresh media (e.g., Ham's F12 media, with 10% FBS, penicillin and streptomycin) is added. The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

PPP1R5 cDNA capable of expressing active PPP1R5 is isolated. The ends of the fragment are modified, if necessary, for cloning into the vector. For instance, 5' overhanging may be treated with DNA polymerase to create blunt ends. 3' overhanging ends may be removed using S1 nuclease. Linkers may be ligated to blunt ends with T4 DNA ligase.

Equal quantities of the Moloney Murine Leukemia Virus linear backbone and the PPP1R5 fragment are mixed together and joined using T4 DNA ligase. The ligation mixture is used to transform *E. coli* and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the PPP1R5 gene is introduced into the packaging cells by standard techniques. Infectious viral particles containing the PPP1R5 gene are collected from the packaging cells, which now are called producer cells.

Fresh media is added to the producer cells, and after an appropriate incubation period, media is harvested from the plates of confluent producer cells. The media, containing the infectious viral particles, is filtered through a MILLIPORE filter (Bedford, Mass.) to remove detached producer cells. The filtered media is then used to infect fibroblast cells. Media is removed from a sub-confluent plate of fibroblasts and quickly replaced with the filtered media. POLYBRENE (Aldrich Chemical Co., Milwaukee, Wis.) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts may then be injected into rats, either alone or after having been grown to confluence on microcarrier beads such as CYTODEX 3 beads. The injected fibroblasts produce PPP1R5 product, and the biological actions of the protein are conveyed to the host.

It will be clear that the invention may be practiced otherwise than as particularly described in the foregoing description and examples. Numerous modifications and variations of the present invention are possible in light of the above teachings and, therefore, are within the scope of the appended claims.

What is claimed is:

1. An isolated polynucleotide fragment comprising a nucleotide sequence encoding a polypeptide comprising the amino acid sequence of SEQ ID NO: 2.

2. The polynucleotide of claim 1 wherein the polynucleotide is DNA or RNA.

3. The polynucleotide of claim 2 comprising the nucleotide sequence set forth in SEQ ID NO: 1.

4. The polynucleotide of claim 2 comprising nucleotides 1–1158 set forth in SEQ ID NO: 1.

5. The polynucleotide of claim 2 which encodes a polypeptide comprising the amino acid sequence of SEQ ID NO: 2.

6. An isolated vector comprising the DNA of claim 2.

7. An isolated host cell comprising the vector of claim 6.

8. A process for producing a PPP1R5 polypeptide comprising culturing the isolated host cell of claim 7 under conditions sufficient for the production of said polypeptide and recovering the polypeptide from the culture.

9. A process for producing a cell which expresses a polypeptide comprising transforming or transfecting the cell with the vector of claim 6 such that the cell expresses the polypeptide encoded by the human cDNA contained in the vector.

10. The isolated polynucleotide of claim 1 comprising a nucleotide sequence encoding the polypeptide as set forth in SEQ ID NO: 2.

11. The isolated polynucleotide of claim 1 comprising a nucleotide sequence encoding the polypeptide comprising amino acids 1 to 317 of SEQ ID NO:2.

12. The isolated polynucleotide of claim 1 comprising a nucleotide sequence encoding the polypeptide comprising amino acids 6 to 317 of SEQ ID NO:2.

13. The isolated polynucleotide of claim 1 comprising a nucleotide sequence encoding the polypeptide comprising amino acids 20 to 317 of SEQ ID NO:2.

14. The isolated polynucleotide of claim 1 comprising a polynucleotide encoding the polypeptide comprising amino acids 26 to 317 of SEQ ID NO:2.

15. The isolated polynucleotide of claim 1 comprising a nucleotide sequence encoding a polypeptide having at least 100 contiguous amino acids from the amino acid sequence set forth in SEQ ID NO:2, wherein said polypeptide binds PP1.

16. The isolated polynucleotide of claim 1 comprising a nucleotide sequence encoding a polypeptide having at least 200 contiguous amino acids from the amino acid sequence set forth in SEQ ID NO:2, wherein said polypeptide binds PP1.

17. The isolated polynucleotide of claim 1 wherein said nucleotide sequence is the entire length of the RNA transcript of SEQ ID NO:1.

18. The isolated polynucleotide of claim 1 wherein said nucleotide sequence is the coding region of the RNA transcript of SEQ ID NO:1.

19. An isolated expression vector comprising a polynucleotide encoding a polypeptide comprising the amino acid sequence set forth in SEQ ID NO: 2.

20. A process for producing a cell which produces a PP1R5 polypeptide thereof comprising transforming or transfecting a host cell with the expression vector of claim 19 such that the host cell, under appropriate culture conditions, produces a PPP1R5 polypeptide.

21. An isolated polynucleotide sequence which is complementary to any of the isolated polynucleotides in any one of claims 1–5, 10, 11–14, 15–16, 17–18, or 19.

* * * * *

```
                          SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
           (A) LENGTH: 1158 base pairs
           (B) TYPE: nucleic acid
           (C) STRANDEDNESS: double
           (D) TOPOLOGY: linear (ii) MOLECULE TYPE: cDNA (ix) FEATURE:
           (A) NAME/KEY: CDS
           (B) LOCATION: 92..1042

(xi) SEQUENCE DESCRIPTION: SEQ ID NO:1:

CACGAGGCCG CGGGGGCAAG GCCTGGAGCT GTGGTTCGAA TTTGTGCAGG CAGCGGGTGC       60

TGGCTTTTAG GGTCCGCCGC CTCTCTGCCT A ATG AGC TGC ACC AGA ATG ATC        112
                                      Met Ser Cys Thr Arg Met Ile
                                        1               5

CAG GTT TTA GAT CCA CGT CCT TTG ACA AGT TCG GTC ATG CCC GTG GAT       160
   Gln Val Leu Asp Pro Arg Pro Leu Thr Ser Ser Val Met Pro Val Asp
                10                  15                  20

GTG GCC ATG AGG CTT TGC TTG GCA CAT TCA CCA CCT GTG AAG AGT TTC       208
   Val Ala Met Arg Leu Cys Leu Ala His Ser Pro Pro Val Lys Ser Phe
       25                  30                  35

CTG GGC CCG TAC GAT GAA TTT CAA CGA CGA CAT TTT GTG AAT AAA TTA       256
   Leu Gly Pro Tyr Asp Glu Phe Gln Arg Arg His Phe Val Asn Lys Leu
   40                  45                  50                  55

AAG CCC CTG AAA TCA TGT CTC AAT ATA AAA CAC AAA GCC AAA TCA CAG       304
   Lys Pro Leu Lys Ser Cys Leu Asn Ile Lys His Lys Ala Lys Ser Gln
                   60                  65                  70

AAT GAC TGG AAG TGC TCA CAC AAC CAA GCC AAG AAG CGC GTT GTG TTT       352
   Asn Asp Trp Lys Cys Ser His Asn Gln Ala Lys Lys Arg Val Val Phe
               75                  80                  85

GCT GAC TCC AAG GGC CTC TCT CTC ACT GCG ATC CAT GTC TTC TCC GAC       400
   Ala Asp Ser Lys Gly Leu Ser Leu Thr Ala Ile His Val Phe Ser Asp
           90                  95                 100

CTC CCA GAA GAA CCA GCG TGG GAT CTG CAG TTT GAT CTC TTG GAC CTT       448
   Leu Pro Glu Glu Pro Ala Trp Asp Leu Gln Phe Asp Leu Leu Asp Leu
       105                 110                 115

AAT GAT ATC TCC TCT GCC TTA AAA CAC CAC GAG GAG AAA AAC TTG ATT       496
   Asn Asp Ile Ser Ser Ala Leu Lys His His Glu Glu Lys Asn Leu Ile
   120                 125                 130                 135

TTA GAT TTC CCT CAA CCT TCA ACC GAT TAC TTA AGT TTC CGG AGC CAC       544
   Leu Asp Phe Pro Gln Pro Ser Thr Asp Tyr Leu Ser Phe Arg Ser His
                   140                 145                 150

TTT CAG AAG AAC TTT GTC TGT CTG GAG AAC TGC TCA TTG CAA GAG CGA       592
   Phe Gln Lys Asn Phe Val Cys Leu Glu Asn Cys Ser Leu Gln Glu Arg
               155                 160                 165
```

```
ACA GTG ACA GGG ACT GTT AAA GTC AAA AAT GTG AGT TTT GAG AAG AAA        640
Thr Val Thr Gly Thr Val Lys Val Lys Asn Val Ser Phe Glu Lys Lys
            170                 175                 180

GTT CAG ATC CGT ATC ACT TTC GAT TCT TGG AAA AAC TAC ACT GAC GTA        688
Val Gln Ile Arg Ile Thr Phe Asp Ser Trp Lys Asn Tyr Thr Asp Val
185                 190                 195

GAC TGT GTC TAT ATG AAA AAT GTG TAT GGT GGC ACA GAT AGT GAT ACC        736
Asp Cys Val Tyr Met Lys Asn Val Tyr Gly Gly Thr Asp Ser Asp Thr
200                 205                 210                 215

TTC TCA TTT GCC ATT GAC TTA CCC CCT GTC ATT CCA ACT GAG CAG AAA        784
Phe Ser Phe Ala Ile Asp Leu Pro Pro Val Ile Pro Thr Glu Gln Lys
            220                 225                 230

ATT GAG TTC TGC ATT TCT TAC CAT GCT AAT GGG CAA GTC TTT TGG GAC        832
Ile Glu Phe Cys Ile Ser Tyr His Ala Asn Gly Gln Val Phe Trp Asp
            235                 240                 245

AAC AAT GAT GGT CAG AAT TAT AGA ATT GTT CAT GTT CAA TGG AAG CCT        880
Asn Asn Asp Gly Gln Asn Tyr Arg Ile Val His Val Gln Trp Lys Pro
            250                 255                 260

GAT GGG GTG CAG ACA CAG ATG GCA CCC CAG GAC TGT GCA TTC CAC CAG        928
Asp Gly Val Gln Thr Gln Met Ala Pro Gln Asp Cys Ala Phe His Gln
265                 270                 275

ACG TCT CCT AAG ACA GAG TTA GAG TCA ACA ATC TTT GGC AGT CCG AGG        976
Thr Ser Pro Lys Thr Glu Leu Glu Ser Thr Ile Phe Gly Ser Pro Arg
280                 285                 290                 295

CTG GCT AGT GGG CTC TTC CCA GAG TGG CAG AGC TGG GGG AGA ATG GAG       1024
Leu Ala Ser Gly Leu Phe Pro Glu Trp Gln Ser Trp Gly Arg Met Glu
            300                 305                 310

AAC TTG GCC TCT TAT CGA TGAATTAAGC AACAATGTAA CTGGTCTTGA              1072
Asn Leu Ala Ser Tyr Arg
            315

CTTGTCATAT TCCCCCATGC AATCCTAGGT CTGTATTGCT CAATTTTAGG AAGCCTTTGC     1132

TACTCCATCA GTAGGTTTAG ATTTGA                                          1158

(2) INFORMATION FOR SEQ ID NO:2:

(i) SEQUENCE CHARACTERISTICS:
        (A) LENGTH: 317 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Cys Thr Arg Met Ile Gln Val Leu Asp Pro Arg Pro Leu Thr
1               5                   10                  15

Ser Ser Val Met Pro Val Asp Val Ala Met Arg Leu Cys Leu Ala His
                20                  25                  30

Ser Pro Pro Val Lys Ser Phe Leu Gly Pro Tyr Asp Glu Phe Gln Arg
            35                  40                  45

Arg His Phe Val Asn Lys Leu Lys Pro Leu Lys Ser Cys Leu Asn Ile
        50                  55                  60

Lys His Lys Ala Lys Ser Gln Asn Asp Trp Lys Cys Ser His Asn Gln
65                  70                  75                  80

Ala Lys Lys Arg Val Val Phe Ala Asp Ser Lys Gly Leu Ser Leu Thr
                85                  90                  95

Ala Ile His Val Phe Ser Asp Leu Pro Glu Glu Pro Ala Trp Asp Leu
            100                 105                 110

Gln Phe Asp Leu Leu Asp Leu Asn Asp Ile Ser Ser Ala Leu Lys His
        115                 120                 125
```

```
His Glu Glu Lys Asn Leu Ile Leu Asp Phe Pro Gln Pro Ser Thr Asp
                130                 135                 140

Tyr Leu Ser Phe Arg Ser His Phe Gln Lys Asn Phe Val Cys Leu Glu
145                 150                 155                 160

Asn Cys Ser Leu Gln Glu Arg Thr Val Thr Gly Thr Val Lys Val Lys
                165                 170                 175

Asn Val Ser Phe Glu Lys Lys Val Gln Ile Arg Ile Thr Phe Asp Ser
                180                 185                 190

Trp Lys Asn Tyr Thr Asp Val Asp Cys Val Tyr Met Lys Asn Val Tyr
                195                 200                 205

Gly Gly Thr Asp Ser Asp Thr Phe Ser Phe Ala Ile Asp Leu Pro Pro
                210                 215                 220

Val Ile Pro Thr Glu Gln Lys Ile Glu Phe Cys Ile Ser Tyr His Ala
225                 230                 235                 240

Asn Gly Gln Val Phe Trp Asp Asn Asn Asp Gly Gln Asn Tyr Arg Ile
                245                 250                 255

Val His Val Gln Trp Lys Pro Asp Gly Val Gln Thr Gln Met Ala Pro
                260                 265                 270

Gln Asp Cys Ala Phe His Gln Thr Ser Pro Lys Thr Glu Leu Glu Ser
                275                 280                 285

Thr Ile Phe Gly Ser Pro Arg Leu Ala Ser Gly Leu Phe Pro Glu Trp
                290                 295                 300

Gln Ser Trp Gly Arg Met Glu Asn Leu Ala Ser Tyr Arg
305                 310                 315

(2) INFORMATION FOR SEQ ID NO:3:

(i) SEQUENCE CHARACTERISTICS:
        (A) LENGTH: 284 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

Met Ala Val Asp Ile Glu Tyr Ser Tyr Ser Ser Met Ala Pro Ser Leu
1               5                   10                  15

Arg Arg Glu Arg Phe Thr Phe Lys Ile Ser Pro Lys Leu Asn Lys Pro
                20                  25                  30

Leu Arg Pro Cys Ile Gln Leu Gly Ser Lys Asp Glu Ala Gly Arg Met
                35                  40                  45

Val Ala Pro Thr Val Gln Glu Lys Lys Val Lys Lys Arg Val Ser Phe
50                  55                  60

Ala Asp Asn Gln Gly Leu Ala Leu Thr Met Val Lys Val Phe Ser Glu
65                  70                  75                  80

Phe Asp Asp Pro Leu Asp Ile Pro Phe Asn Ile Thr Glu Leu Leu Asp
                85                  90                  95

Asn Ile Val Ser Leu Thr Thr Ala Glu Ser Glu Ser Phe Val Leu Asp
                100                 105                 110

Phe Pro Gln Pro Ser Ala Asp Tyr Leu Asp Phe Arg Asn Arg Leu Gln
                115                 120                 125

Thr Asn His Val Cys Leu Glu Asn Cys Val Leu Lys Glu Lys Ala Ile
                130                 135                 140

Ala Gly Thr Val Lys Val Gln Asn Leu Ala Phe Glu Lys Val Val Lys
145                 150                 155                 160
```

```
Ile Arg Met Thr Phe Asp Thr Trp Lys Ser Phe Thr Asp Phe Pro Cys
                165                 170                 175

Gln Tyr Val Lys Asp Thr Tyr Ala Gly Ser Asp Arg Asp Thr Phe Ser
            180                 185                 190

Phe Asp Ile Ser Leu Pro Glu Lys Ile Gln Ser Tyr Glu Arg Met Glu
                195                 200                 205

Phe Ala Val Cys Tyr Glu Cys Asn Gly Gln Ser Tyr Trp Asp Ser Asn
            210                 215                 220

Lys Gly Lys Asn Tyr Arg Ile Thr Arg Ala Glu Leu Arg Ser Thr Gln
225                 230                 235                 240

Gly Met Thr Glu Pro Tyr Asn Gly Pro Asp Phe Gly Ile Ser Phe Asp
                245                 250                 255

Gln Phe Gly Ser Pro Arg Cys Ser Phe Gly Leu Phe Pro Glu Trp Pro
                260                 265                 270

Ser Tyr Leu Gly Tyr Glu Lys Leu Gly Pro Tyr Tyr
                275                 280

(2) INFORMATION FOR SEQ ID NO:4:

(i) SEQUENCE CHARACTERISTICS:
        (A) LENGTH: 102 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

Ala Ile Leu Glu Ser Thr Glu Ser Leu Leu Gly Ser Thr Ser Ile Lys
1               5                   10                  15

Gly Ile Ile Arg Val Leu Asn Val Ser Phe Glu Lys Leu Val Tyr Val
                20                  25                  30

Arg Met Ser Leu Asp Asp Trp Gln Thr His Tyr Asp Ile Leu Ala Glu
            35                  40                  45

Tyr Val Pro Asn Ser Cys Asp Gly Glu Thr Asp Gln Phe Ser Phe Lys
50                  55                  60

Ile Val Leu Val Pro Pro Tyr Gln Lys Asp Gly Ser Lys Val Glu Phe
65                  70                  75                  80

Cys Ile Arg Tyr Glu Thr Ser Val Gly Thr Phe Trp Ser Asn Asn Asn
                85                  90                  95

Gly Thr Asn Tyr Thr Phe
                100

(2) INFORMATION FOR SEQ ID NO:5:

(i) SEQUENCE CHARACTERISTICS:
        (A) LENGTH: 117 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

Val Lys Leu His Ser Leu Thr Gln Leu Gly Asp Asp Ser Ser Lys Ile
1               5                   10                  15

Thr Gly Leu Val Tyr Val Lys Asn Leu Ser Phe Glu Lys Tyr Leu Glu
                20                  25                  30

Ile Lys Phe Thr Phe Asn Ser Trp Arg Asp Ile His Tyr Val Thr Ala
            35                  40                  45
```

```
Asn Phe Asn Arg Thr Ile Asn Ser Asn Val Asp Glu Phe Lys Phe Thr
    50                  55                  60

Ile Asp Leu Asn Ser Leu Lys Tyr Ile Leu Leu Ile Lys Arg Ile Ile
65                  70                  75                  80

Thr Met Glu Lys Asn Thr Ser Ser Cys Pro Leu Asn Ile Glu Leu Cys
                85                  90                  95

Cys Arg Tyr Asp Val Asn Asn Glu Thr Tyr Tyr Asp Asn Asn Asn Gly
                100                 105                 110

Lys Asn Tyr His Leu
            115

(2) INFORMATION FOR SEQ ID NO:6:

(i) SEQUENCE CHARACTERISTICS:
        (A) LENGTH: 96 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Val Gln Leu Asp Ser Tyr Asn Tyr Asp Gly Ser Thr Phe Ser Gly Lys
1               5                   10                  15

Ile Tyr Val Lys Asn Ile Ala Tyr Ser Lys Lys Val Thr Val Ile Tyr
                20                  25                  30

Ala Asp Gly Ser Asp Asn Trp Asn Asn Asn Gly Asn Thr Ile Ala Ala
            35                  40                  45

Ser Tyr Ser Ala Pro Ile Ser Gly Ser Asn Tyr Glu Tyr Trp Thr Phe
    50                  55                  60

Ser Ala Ser Ile Asn Gly Ile Lys Glu Phe Tyr Ile Lys Tyr Glu Val
65                  70                  75                  80

Ser Gly Lys Thr Tyr Tyr Asp Asn Asn Asn Ser Ala Asn Tyr Gln Val
                85                  90                  95
```